(12) United States Patent
Guyon et al.

(10) Patent No.: US 8,543,519 B2
(45) Date of Patent: Sep. 24, 2013

(54) SYSTEM AND METHOD FOR REMOTE MELANOMA SCREENING

(75) Inventors: Isabelle Guyon, Berkeley, CA (US); Stephen D. Barnhill, Savannah, GA (US)

(73) Assignee: Health Discovery Corporation, Atlanta, GA (US)

(*) Notice: Subject to any disclaimer, the term of this patent is extended or adjusted under 35 U.S.C. 154(b) by 134 days.

(21) Appl. No.: 12/975,306

(22) Filed: Dec. 21, 2010

(65) Prior Publication Data

US 2012/0008838 A1    Jan. 12, 2012

Related U.S. Application Data

(63) Continuation-in-part of application No. 12/814,431, filed on Jun. 11, 2010, now Pat. No. 8,275,723, which is a continuation of application No. 11/926,129, filed on Oct. 29, 2007, now Pat. No. 7,797,257, which is a continuation of application No. 11/033,570, filed on Jan. 11, 2005, which is a continuation of application No. 09/633,410, filed on Aug. 7, 2000, now Pat. No. 6,882,990.

(60) Provisional application No. 61/289,372, filed on Dec. 22, 2009, provisional application No. 61/293,987, filed on Jan. 11, 2010, provisional application No. 61/304,796, filed on Feb. 15, 2010, provisional application No. 61/308,792, filed on Feb. 26, 2010.

(51) Int. Cl.
*G06F 15/18* (2006.01)

(52) U.S. Cl.
USPC .......................................................... 706/12

(58) Field of Classification Search
USPC .......................................................... 706/12
See application file for complete search history.

(56) References Cited

U.S. PATENT DOCUMENTS

| | | | |
|---|---|---|---|
| 4,881,178 A | 11/1989 | Holland et al. |
| 5,138,694 A | 8/1992 | Hamilton et al. |
| 5,649,068 A | 7/1997 | Boser et al. |
| 5,809,144 A | 9/1998 | Sirbu et al. |
| 5,878,746 A | 3/1999 | Lemelson et al. |
| 5,950,146 A | 9/1999 | Vapnik |

(Continued)

OTHER PUBLICATIONS

International Search Report and Written Opinion for PCT/US2010/061667 issued Aug. 19, 2011, 8 pages.

(Continued)

*Primary Examiner* — Michael B Holmes
(74) *Attorney, Agent, or Firm* — Eleanor M. Musick; Procopio, Cory, Hargreaves & Savitch LLP

(57) ABSTRACT

A system and method are provided for diagnosing diseases or conditions from digital images taken by a remote user with a smart phone or a digital camera and transmitted to an image analysis server in communication with a distributed network. The image analysis server includes a trained learning machine for classification of the images. The user-provided image is pre-processed to extract dimensional, shape and color features then is processed using the trained learning machine to classify the image. The classification result is postprocessed to generate a risk score that is transmitted to the remote user. A database associated with the server may include referral information for geographically matching the remote user with a local physician. An optional operation includes collection of financial information to secure payment for analysis services.

13 Claims, 20 Drawing Sheets

(56) References Cited

U.S. PATENT DOCUMENTS

| | | | |
|---|---|---|---|
| 6,021,344 A * | 2/2000 | Lui et al. | 600/476 |
| 6,128,608 A | 10/2000 | Barnhill | |
| 6,157,921 A | 12/2000 | Barnhill | |
| 6,161,130 A | 12/2000 | Horvitz et al. | |
| 6,248,063 B1 | 6/2001 | Barnhill et al. | |
| 6,282,523 B1 | 8/2001 | Tedesco et al. | |
| 6,306,087 B1 | 10/2001 | Barnhill et al. | |
| 6,411,936 B1 * | 6/2002 | Sanders | 705/7.32 |
| 6,427,141 B1 | 7/2002 | Barnhill | |
| 6,553,358 B1 | 4/2003 | Horvitz | |
| 6,608,628 B1 * | 8/2003 | Ross et al. | 345/619 |
| 6,658,395 B1 | 12/2003 | Barnhill | |
| 6,714,925 B1 | 3/2004 | Barnhill | |
| 6,760,715 B1 | 7/2004 | Barnhill | |
| 6,789,069 B1 | 9/2004 | Barnhill | |
| 6,882,990 B1 | 4/2005 | Barnhill et al. | |
| 6,996,549 B2 * | 2/2006 | Zhang et al. | 706/16 |
| 7,117,188 B2 | 10/2006 | Guyon et al. | |
| 7,383,237 B2 | 6/2008 | Zhang et al. | |
| 7,389,306 B2 | 6/2008 | Schuetze et al. | |
| 7,444,308 B2 | 10/2008 | Guyon et al. | |
| 7,542,947 B2 | 6/2009 | Guyon et al. | |
| 7,542,999 B2 | 6/2009 | Kamath et al. | |
| 7,551,780 B2 | 6/2009 | Nudd et al. | |
| 7,587,412 B2 | 9/2009 | Weyl et al. | |
| 7,639,387 B2 | 12/2009 | Hull et al. | |
| 7,669,148 B2 | 2/2010 | Hull et al. | |
| 7,672,543 B2 | 3/2010 | Hull et al. | |
| 7,702,673 B2 | 4/2010 | Hull et al. | |
| 7,797,257 B2 | 9/2010 | Barnhill et al. | |
| 8,008,012 B2 * | 8/2011 | Guyon | 435/6.14 |
| 8,275,723 B2 * | 9/2012 | Barnhill et al. | 706/13 |
| 8,293,469 B2 * | 10/2012 | Guyon | 435/6.1 |
| 2008/0161661 A1 | 7/2008 | Gizewski | |
| 2008/0226151 A1 | 9/2008 | Zouridakis et al. | |
| 2008/0275315 A1 | 11/2008 | Oka et al. | |
| 2009/0154781 A1 | 6/2009 | Bogdan | |

OTHER PUBLICATIONS

Begelman, G. et al, "A Microscopic Telepathology System for Multiresolution Computer-Aided Diagnostics", Journal of Multimedia, Dec. 2006, pp. 40-48, vol. 1, No. 7.

Iyatomi, H., et al., "An Internet-based Melanoma Diagnostic System—Towad the Practical Application", Proceedings of the 2005 IEEE Symposium on Computational Intelligence in Bioinformatics and Computational Biology, 2005, pp. 1-4.

Iyatomi, H., et al., "Parameterization of Dermoscopic Findings for the Internet-based Melanoma Screening System", Proceedings of the 2007 IEEE Symposium on Computational Intelligence in Image and Signal Processing (CIISP 2007), 2007, pp. 189-193.

Iyatomi, H., et al., "An Internet-based Melanoma Screening System with Acral Volar Lesion Support", Proc. of the 30th Annual International Conference of the IEEE Engineering in Medicine and Biology Society (EMBC 2008), Aug. 2008, pp. 5156-5159.

Iyatomi, H., et al., "An Internet-based melanoma screening system with dermatologist-like tumor area extraction algorithm", Computerized Medical Imaging and Graphics, 2008, pp. 566-579, vol. 32.

Ogorzalek, M.J., et al., "New Approaches for Computer-Assisted Skin Cancer Diagnosis", The Third International Symposium on Optimization and Systems Biology (OSB '09), China, Sep. 2009, pp. 65-72.

Yuan, X., et al, "SVM-based Texture Classification and Application to Early Melanoma Detection", Proceedings of the 28th IEEE EMBS Annual International Conference, New York City, Aug. 30-Sep. 3, 2006, pp. 4775-4778.

Celebi, M.E., et al., "Detection of Blue-White Veil Areas in Dermoscopy Images Using Machine Learning Techniques", SPIE Medical Imaging 2006: Image Processing, 2006, vol. 6144.

Guyon, I., et al., "An Introduction to Variable and Feature Selection", Journal of Machine Learning Research, 2003, pp. 1157-1182, vol. 3.

Guyon, I., et al., "Gene Selection for Cancer Classification using Support Vector Machines", Machine Learning, 2002, pp. 389-422, vol. 46.

Arodz, Tomasz, et al., "Detection of clustered microcalcifications in small field digital mammography", Computer Methods and Programs in Biomedicine, 2006, vol. 81, pp. 56-65.

Campanini, Renato, et al., "A novel featureless approach to mass detection in digital mammograms based on Support Vector Machines", Physics in Medicine and Biology, Mar. 2004, vol. 49(6): 961-976.

Masotti, "Exploring Ranklets Performances in Mammographic Mass Classification Using Recursive Feature Elimination," Submitted to International Conf. on Image Processing 2005, Sep. 11-14, Genova, Italy.

Acha, Begona, et al., "Classification of burn wounds using support vector machines", SPIE Medical Imaging 2004: Image Processing, vol. 5370. pp. 1118-1025. San Diego. Feb. 2004.

iPhone Body Mole App Zooms in on Skin Cancer, iPhone Savior. com, 2009.

* cited by examiner

SYSTEM AND METHOD FOR REMOTE MELANOMA SCREENING

RELATED APPLICATIONS

This application claims the priority of each of U.S. Provisional Application No. 61/289,372, filed Dec. 22, 2009, U.S. Provisional Application No. 61/293,987, filed Jan. 11, 2010, U.S. Provisional Application No. 61/304,796, filed Feb. 15, 2010, and U.S. Provisional Application No. 61/308,792, filed Feb. 26, 2010, and is a continuation-in-part of U.S. application Ser. No. 12/814,431, filed Jun. 11, 2010, which is a continuation of application Ser. No. 11/926,129, filed Oct. 29, 2007, now issued as U.S. Pat. No. 7,797,257, which is a continuation of U.S. application Ser. No. 11/033,570, filed Jan. 11, 2005, which is a continuation of U.S. application Ser. No. 09/633,410, filed Aug. 7, 2000, now issued as U.S. Pat. No. 6,882,990. The disclosure of each of the related applications is incorporated herein by reference.

FIELD OF THE INVENTION

The present invention relates to a system and method for computer image analysis for screening for skin cancer using photographic images transmitted over a distributed network from a remote location, and more particularly to a system and method for photographing and downloading images of potential melanoma lesions for processing using learning machines to provide a preliminary risk assessment of melanoma.

BACKGROUND OF THE INVENTION

Malignant melanoma is currently one of the leading cancers among many light-skinned populations around the world. Changes in recreational behavior together with the increase in ultraviolet radiation due to thinning or lost of the earth's ozone layer have caused a dramatic increase in the number of melanomas diagnosed. The rise in incidence was first noticed in the United States in 1930, where one person out of 100,000 per year suffered from skin cancer. This rate increased in the mid-eighties to six per 100,000 and to 13 per 100,000 in 1991. In fact, melanoma is currently one of the most common cancers in young adults. Each year, more than 50,000 people in the U.S. learn that they have melanoma. According to the World Health Organization website, 132,000 new cases of melanoma skin cancer occur globally each year. One in every three cancers diagnosed is a skin cancer and, according to Skin Cancer Foundation Statistics, one in every five Americans will develop skin cancer during their lifetime. Melanoma accounts for about three percent of skin cancer cases, but it causes more than 75 percent of skin cancer deaths. According to the National Cancer Institute, 68,720 new cases and 8,650 deaths from melanoma occurred in the United States in 2009. According to the Vanderbilt Ingram cancer center, Melanoma is among the 5 top most frequently treated cancers (among 20,000 patients).

The importance of early detection of melanoma cannot be overstated. When melanoma is found and treated early, the chances for long-term survival are excellent. Five-year survival rates for patients with early-stage (Stage I) melanoma exceed 90 to 95%. As melanoma progresses, it becomes increasingly more devastating and deadly. In later-stage disease, 5-year survival rates drop to less than 50%. With early detection, however, survival rates have improved steadily in recent years, and 85% of diagnosed patients enjoy long-term survival after simple tumor surgery.

Melanoma starts in the pigment-producing skin cells (melanocytes). The first sign of melanoma is often a change in the size, shape, or color of an existing mole or the appearance of a new mole. Since the vast majority of primary melanomas are visible on the skin, there is a good chance of detecting the disease in its early stages. If not detected at treated at an early stage, these cells become abnormal, grow uncontrollably, and aggressively invade surrounding tissues. Melanoma can spread quickly and produce large malignant tumors in the brain, lung, liver, or other organs, with depth of penetration being predictive of prognosis: Epidermis only: Clark level I. Upper dermis: Clark levels II and II. Lower dermis: Clark level IV. Fatty layers: Clark level V.

Most tumors of the skin are not cancerous and rarely turn into cancer. Skin cancers are divided into non-melanomas and melanomas. Non-melanomas (usually basal cell and squamous cell cancers) are the most common cancers of the skin. Because they rarely spread elsewhere in the body, they are less worrisome than melanomas. Melanoma is much less common than basal cell and squamous cell skin cancers, but it is far more serious. Because it begins in the melanocytes, most of these cells keep on making melanin thus melanoma tumors are often brown or black (but not always). Melanoma most often appears on the trunk of fair-skinned men and on the lower legs of fair-skinned women, but it can appear in other places as well.

The gold standard for accurate diagnosis remains histological examination of biopsies. The type of biopsy depends on the size of the skin growth and its location on the body. Several types of biopsy can be done when melanoma is suspected. The first is an excisional biopsy, which cuts away the entire growth with a margin of normal surrounding skin. A second type is an incisional biopsy, or core biopsy, removing only a sample of the growth. A punch biopsy removes a small, cylindrical shaped sample of skin. A fourth type is a saucerization biopsy, which removes the entire lesion by cutting under the lesion in a "scoop like" manner. A fifth type is a fine-needle aspiration biopsy done with a very thin needle, which removes a very small sample of tissue (usually not done on moles but on other deeper tissue, such as nearby lymph nodes). Prognosis is assessed by the TNM system (T stands for tumor thickness and how far it has spread; N stands for lymph nodes, and whether the tumor has spread to the nodes; and M stands of metastasis, and whether the tumor has spread to distant organs).

Melanoma may also be diagnosed, to some extent, from the appearance of the skin surface. Four main features of the appearance are used: asymmetry, uneven edges, multiple shades, and size. These characteristics, known as the "ABCD" characteristics, provide a subjective means for physicians and patients to identify pigmented skin lesions that could be melanoma. The four parameters represented by the ABCD characteristics are lesion asymmetry (A), border irregularity (B), color variegation (C) and lesion diameter (D). Currently, experienced dermatologists can identify a melanoma with around 75% accuracy (Serruys, 1999).

The ability to identify most melanomas visually suggests that digital images and computer based image analysis may be effective tools for rapid screening. One example of such a tool is the MelaFind® scanner from Electro-Optical Sciences, Inc. (Irvington, N.Y.), aspects of which are described in U.S. Pat. No. 6,081,612, U.S. Pat. No. 6,208,749, U.S. Pat. No. 6,307,957, U.S. Pat. No. 6,563,616, U.S. Pat. No. 6,626,558, U.S. Pat. No. 6,657,798, U.S. Pat. No. 6,710,947, U.S. Pat. No. 7,102,672, and U.S. Pat. No. 7,127,094, filed Jan. 2, 2003, and U.S. Patent Publications No. 2008/0031537, No. 2008/0214907, No. 2008/0312952, No. 2009/0060304 and No. 2009/0154781, each incorporated here by reference. The MelaFind® scanner is a large hand-held scanner housing a multi-spectral light source and a sensor that is placed directly in contact with the lesion. The MelaFind® scanner is designed for use by medical professionals and is not intended for general consumer use, which means that the patient must have already suspected a problem and consulted a physician before such a scanner would be available for use on the patient.

Reported efforts to develop methods for machine-based diagnosis of melanoma using digital images include a number of pre-processing steps, such as standardizing illumination, shading correction, noise filtering for color quality and use of polarizing filters. The image resolution varies from study to study, but typically is not lower than 256×256 pixel images, with 0.01 cm/pixel and 24 bit per pixel color depth. Some methods remove hair by image processing, while others involve shaving the patients around the lesion before taking the photograph.

Accessibility of machine-based diagnosis can be extended by using everyday digital images, such as images taken using the built-in camera of a smart phone or a simple digital camera. Such an approach would make melanoma screening more accessible to individuals who are concerned about the health of their skin but have not yet been able to consult a physician. However, the quality of such images tends to be fairly low.

Optimized extraction and reconstruction of data within an image can be problematic where sources of noise and other factors can negatively impact the ability to efficiently extract data from the image, thus impairing the effectiveness of the imaging method for its intended use. Examples of areas in which image analysis can be problematic include astronomical observation and planetary exploration, where sources can be faint and atmospheric interference introduce noise and distortion, military and security surveillance, where light can be low and rapid movement of targets result in low contrast and blur, and medical imaging, which often suffers from low contrast, blur and distortion due to source and instrument limitations. Adding to the difficulty of image analysis is the large volume of data contained within a digitized image, since the value of any given data point often cannot be established until the entire image is processed.

Development of methods for automated analysis of digital images has received considerable attention over that past few decades, with one of the key areas of interest being the medical field. Applications include analysis of pathology images generated using visual, ultrasound, x-ray, positron emission, magnetic resonance and other imaging methods. As in the case of human-interpreted medical images, an automated image analyzer must be capable of recognizing and classifying blurred features within the images, which often requires discrimination of faint boundaries between areas differing by only a few gray levels or shades of color.

In recent years, machine-learning approaches for image analysis have been widely explored for recognizing patterns which, in turn, allow extraction of significant features within an image from a background of irrelevant detail. Learning machines comprise algorithms that may be trained to generalize using data with known outcomes. Trained learning machine algorithms may then be applied to predict the outcome in cases of unknown outcome. Machine-learning approaches, which include neural networks, hidden Markov models, belief networks and support vector machines, are ideally suited for domains characterized by the existence of large amounts of data, noisy patterns and the absence of general theories. Particular focus among such approaches has been on the application of artificial neural networks to bio-medical image analysis, with results reported in the use of neural networks for analyzing visual images of cytology specimens and mammograms for the diagnosis of breast cancer, classification of retinal images of diabetics, karyotyping (visual analysis of chromosome images) for identifying genetic abnormalities, and tumor detection in ultrasound images, among others.

The majority of learning machines that have been applied to image analysis are neural networks trained using back-propagation, a gradient-based method in which errors in classification of training data are propagated backwards through the network to adjust the bias weights of the network elements until the mean squared error is minimized. A significant drawback of back-propagation neural networks is that the empirical risk function may have many local minimums, a case that can easily obscure the optimal solution from discovery. Standard optimization procedures employed by back-propagation neural networks may converge to a minimum, but the neural network method cannot guarantee that even a localized minimum is attained, much less the desired global minimum. The quality of the solution obtained from a neural network depends on many factors. In particular, the skill of the practitioner implementing the neural network determines the ultimate benefit, but even factors as seemingly benign as the random selection of initial weights can lead to poor results. Furthermore, the convergence of the gradient-based method used in neural network learning is inherently slow. A further drawback is that the sigmoid function has a scaling factor, which affects the quality of approximation. Possibly the largest limiting factor of neural networks as related to knowledge discovery is the "curse of dimensionality" associated with the disproportionate growth in required computational time and power for each additional feature or dimension in the training data.

The shortcomings of neural networks can be overcome by using the support vector machine. In general terms, a support vector machine (SVM) maps input vectors into high dimensional feature space through a non-linear mapping function, chosen a priori. In this high dimensional feature space, an optimal separating hyperplane is constructed. The optimal hyperplane is then used to perform operations such as class separations, regression fit, or density estimation. SVMs are well-recognized as having the advantage in solving classification problems of high dimension and small size dataset.

U.S. Pat. Nos. 6,157,921, 6,714,925, and 7,797,257, which are incorporated herein by reference, describe a system and method for providing SVM analysis services for processing of data transmitted from a remote source over the Internet to a processor that executes trained SVMs. The processor receives the data from the remote source along with account information that provides for a financial transaction to secure payment for the analysis services. Upon completion of the data processing, the analysis results are transmitted to the remote requestor over the Internet and a transaction is initiated, for example with a financial institution, to secure payment for the data analysis services from the designated account.

In view of the serious nature of the disease, and the extreme importance of early detection, a system and method are needed to allow individuals who may be concerned that they have melanoma to obtain a rapid, preliminary screening using a computer-based image analysis and pattern recognition tool that is easily accessible via the Internet and which can utilize readily-available imaging techniques such as a smart phone camera or convention digital camera. The present invention expands the system and method disclosed in the aforementioned patents and applications to provide such a capability.

BRIEF SUMMARY OF THE INVENTION

The present invention relates to systems and methods for enhancing knowledge discovered from data using a learning machine in general, and a support vector machine in particular. In particular, the present invention comprises methods of using a learning machine for diagnosing and prognosing changes in biological systems such as diseases. Further, once the knowledge discovered from the data is determined, the specific relationships discovered are used to diagnose and prognose diseases, and methods of detecting and treating such diseases are applied to the biological system.

One embodiment of the present invention comprises pre-processing a training data set in order to allow the most advantageous application of the learning machine. Each training data point comprises a vector having one or more coordinates. Pre-processing the training data set may comprise identifying missing or erroneous data points and taking appropriate steps to correct the flawed data or as appropriate remove the observation or the entire field from the scope of the problem. Pre-processing the training data set may also comprise adding dimensionality to each training data point by adding one or more new coordinates to the vector. The new coordinates added to the vector may be derived by applying a transformation to one or more of the original coordinates. The transformation may be based on expert knowledge, or may be computationally derived. In a situation where the training data set comprises a continuous variable, the transformation may comprise optimally categorizing the continuous variable of the training data set.

In a preferred embodiment, the support vector machine is trained using the pre-processed training data set. In this manner, the additional representations of the training data provided by the preprocessing may enhance the learning machine's ability to discover knowledge therefrom. In the particular context of support vector machines, the greater the dimensionality of the training set, the higher the quality of the generalizations that may be derived therefrom. When the knowledge to be discovered from the data relates to a regression or density estimation or where the training output comprises a continuous variable, the training output may be post-processed by optimally categorizing the training output to derive categorizations from the continuous variable.

A test data set is pre-processed in the same manner as was the training data set. Then, the trained learning machine is tested using the pre-processed test data set. A test output of the trained learning machine may be post-processed to determine if the test output is an optimal solution. Post-processing the test output may comprise interpreting the test output into a format that may be compared with the test data set. Alternative postprocessing steps may enhance the human interpretability or suitability for additional processing of the output data.

In the context of a support vector machine, also disclosed is a method for the selection of at least one kernel prior to training the support vector machine. The selection of a kernel may be based on prior knowledge of the specific problem being addressed or analysis of the properties of any available data to be used with the learning machine and is typically dependant on the nature of the knowledge to be discovered from the data. Optionally, an iterative process comparing postprocessed training outputs or test outputs can be applied to make a determination as to which configuration provides the optimal solution. If the test output is not the optimal solution, the selection of the kernel may be adjusted and the support vector machine may be retrained and retested. When it is determined that the optimal solution has been identified, a live data set may be collected and pre-processed in the same manner as was the training data set. The pre-processed live data set is input into the learning machine for processing. The live output of the learning machine may then be post-processed by interpreting the live output into a computationally derived alphanumeric classifier or other form suitable to further utilization of the SVM-derived answer.

A system is provided for enhancing knowledge discovered from data using a support vector machine. The exemplary system comprises a storage device for storing a training data set and a test data set, and a processor for executing a support vector machine. The processor is also operable for collecting the training data set from the database, pre-processing the training data set to enhance each of a plurality of training data points, training the support vector machine using the pre-processed training data set, collecting the test data set from the database, pre-processing the test data set in the same manner as was the training data set, testing the trained support vector machine using the pre-processed test data set, and in response to receiving the test output of the trained support vector machine, post-processing the test output to determine if the test output is an optimal solution. The exemplary system may also comprise a communications device for receiving a live data set from a remote source. In such a case, the processor may be operable to store the live data set in the storage device prior pre-processing. The exemplary system may also comprise a display device for displaying the post-processed results. The processor of the exemplary system may further be operable for performing each additional function described above. The communications device may be further operable to send a computationally derived alphanumeric classifier or other raw or post-processed output data to a remote source. In some embodiments, prior to transmitting the result to the customer via the distributed network, the processor may be operable to communicate with a financial institution or other account provider for the purpose of securing payment for analysis services through an account identified by an account identifier provided by the service requester.

A system and method are provided for enhancing knowledge discovery from data using multiple learning machines in general and multiple support vector machines in particular. Multiple support vector machines, each comprising distinct kernels, are trained with the pre-processed training data and are tested with test data that is pre-processed in the same manner. The test outputs from multiple support vector machines may be compared in order to determine which of the test outputs, if any, represents an optimal solution. Selection of one or more kernels may be adjusted and one or more support vector machines may be retrained and retested. When it is determined that an optimal solution has been achieved, live data is pre-processed and input into the support vector machine comprising the kernel(s) that produced the optimal solution. The live output from the learning machine may then be post-processed into a computationally derived alphanumeric classifier for interpretation by a human or computer automated process.

In one aspect of the invention, a system and method are provided for enhancing knowledge discovery from data using a learning machine that is accessible via a distributed network environment, e.g., the Internet. A customer may transmit training data, test data and/or live data to a central server from a remote source over the network. The customer may also transmit to the server identification information such as a user name, a password, geographical location, an account identifier, or the financial account identifier of a third party's account, charges to which are initiated by information entered by the user. In one embodiment, the account identifier is associated with an Internet-enabled smart phone, such as a mobile phone number or wireless service account number, so that billing for analysis services can be charged to the user's mobile phone account. The training data, test data and/or live data may be stored in a storage device at the central server. The learning machine is trained and tested prior to receiving and processing of live data that is transmitted by the remote user.

Training data may be pre-processed in order to add meaning thereto. Pre-processing data may involve transforming the data points and/or expanding the data points. By adding meaning to the data, the learning machine is provided with a greater amount of information for processing. The learning machine, which may be a support vector machine, a random forest classifier, a Gaussian classifier or other classifier, or an ensemble classifier, is trained with the pre-processed training data and is tested with test data that is pre-processed in the same manner. The test output from the learning machine is post-processed in order to determine if the knowledge discovered from the test data is desirable. In other words, the output is evaluated to determine if the correct classification has been made by the learning machine. Post-processing involves interpreting the test output into a format that may be compared with the test data. Once the learning machine has been satisfactorily trained, live data is pre-processed and input into the trained and tested learning machine. The live output from the learning machine may then be post-processed into a computationally derived alphanumerical classifier or converted into a graphical display for easy interpretation by a human.

In one aspect of the invention, a system is provided for analyzing image data received from a remote user for evaluating an image for screening for a disease or condition, the system comprising: a server in communication with a distributed network for receiving a digital image data set from the remote user, the remote user also in communication with the distributed network; a processor for executing a learning machine, wherein the learning machine is trained using image data sets having known outcomes for skin cancer, the processor further operable for: receiving the digital image data set from the remote user; pre-processing the digital image data set to extract from the image; inputting the extracted features into the trained learning machine to produce an output comprising a recognized pattern within the digital image data set; post-processing the output to generate a score corresponding to the recognized pattern associated with the disease or condition; and transmitting the score to the server; wherein the server is further operable for transmitting the score to the remote user across the distributed network.

In a particular application of the learning machine according to the present invention, a system and method are provided for analyzing data comprising a digital image taken by an individual at a remote location who wishes to obtain a preliminary screening for skin cancer such as melanoma.

In another aspect of the invention, a system is provided for analyzing image data received from a remote user for screening for skin cancer, the system comprising: a server in communication with a distributed network for receiving a digital image data set from the remote user, the remote user also in communication with the distributed network; a processor for executing a learning machine, wherein the learning machine is trained using image data sets having known outcomes for skin cancer, the processor further operable for: receiving the digital image data set from the remote user; pre-processing the digital image data set to extract features including contour, dimension and color features; inputting the extracted features into the trained learning machine to produce an output comprising a recognized pattern within the digital image data set; post-processing the output to generate a skin cancer risk score corresponding to the recognized pattern; and transmitting the skin cancer risk score to the server; wherein the server is further operable for transmitting the alphanumerical skin cancer risk score to the remote user across the distributed network.

In a preferred embodiment, the learning machine located at a central server accessible via the Internet is trained and tested for classifying melanoma images using image data obtained and downloaded by the service provider, while the live data is provided by a remote user who is interested in receiving a preliminary screening for melanoma using an automated, computer-based analysis. The sources of the image data for training and testing of the learning machine may include medical literature and image databases on the Internet, diagnostic laboratories and research institutions. The image data will have known classifications based on expert evaluations, i.e., by a pathologist or dermatologist, or a combination of a visual evaluation by a dermatologist and confirmation by a pathologist using histological methods.

In an exemplary embodiment, a method is provided for diagnosing melanoma from digital images taken with a multimedia enabled smart phone or a digital camera and transmitted to a remote central server, e.g., by email or by download to a dedicated website associated with the central server. The user may be requested to enter additional information that can be combined with the image data in the classification process. The user-entered information may include size, shape, color, itching, bleeding, and/or changes over time. The user may also be requested to download additional photographs of other, less worrisome markings (moles) on their skin for comparison. The image is pre-processed to enhance the image quality. Pre-processing may involve actions by the user in response to instructions provided by the system that are intended to optimize the clarity and accuracy of the image. Following user-pre-processing and download, pre-processing may include one or more of segmentation, extraction of contours of inner structure, extraction of geometrical features, and extraction of color features. The features that are evaluated are based on the ABCD scale that is commonly used by dermatologists to diagnose melanoma: asymmetry ("A"), border ("B"), color ("C"), and diameter ("D"). Once the desired features are extracted, a learning machine that has been trained and tested to accurately classify melanoma is used to classify the suspected lesion. Appropriate learning machines for such a task include support vector machines, neural networks, random forests, Bayesian classifiers, other statistically-based classifiers, or other classifiers, or combinations thereof. In the preferred embodiment, a kernel based machine such as a support vector machine is used. In one embodiment, an ensemble of classifiers is used, with each classifier being trained on a different feature set.

The result of each classifier is postprocessed to obtain a mapping of outputs to probabilities. In one embodiment, an ensemble of classifiers is obtained by voting of different base classifiers, with each base classifier being given an equal weight. In another embodiment, a second level, overall or stacking classifier that has been trained to generate a single "diagnosis" based on inputs consisting of the outputs of the different feature classifiers, i.e., ABCD, receives the result from each classifier and generates a score.

The resulting vote (score) of the ensemble or second level classifier is post-processed to obtain a mapping of the output to probabilities. The output is converted into an alphanumeric and/or graphical display that may be stored in a memory medium and/or transmitted to the remote user to provide an overall probability, i.e., a confidence level, that the lesion in the image is melanoma. In a preferred embodiment, explanatory language may be included within the transmitted graphical display. In addition, referral suggestions may be provided based upon the user's geographical location, which may be obtained from a smart phone with location services, e.g., GPS capability, if available and accessible to the central server, or by requesting that the user input information such as the zip code, area code or city/state/country in which they are located. Once the user's location information is received, which may be at the beginning or end of the sequence of image processing and classification operations, the central server can access and search a database of qualified physicians or medical facilities within the same city or geographical area that can provide further evaluation and/or treatment of the user's possible condition. If the system's analysis of the transmitted photograph of the area of concern indicates an elevated risk level, the system will identify one or more physicians within the sender's area and will transmit contact information for the physician at the same time the sender's risk level is sent.

In one embodiment, the sender will be charged a nominal fee for the analysis of the transmitted image by requesting credit or debit card information or providing some other on-line payment mechanism such as PayPal® or similar Internet-based transaction services. Alternatively, the billing may be enabled via a contract between the analysis service provider and the wireless service provider, e.g., as a data charge that can be included on the user's wireless billing statement. A typical fee may be on the order of $2 to $20. The rationale for charging such a fee would be that the persons using the service would genuinely be interested in obtaining the analysis, as opposed to people who are simply taking advantage of a free service or "playing", without having a genuine need for the screening services. Alternatively, no fee will be charged to the user, and the database can instead include listings of physicians who will be charged a fee for each referral. When a particular physician is recommended to the remote user, that physician would be charged a fee. In addition, or in lieu of either alternative, the service could be fully paid for by a diagnostic laboratory and the database would include a listing of physicians who contract with that diagnostic laboratory for skin cancer diagnostics such that the diagnostic laboratory would benefit by ultimately receiving the request for pathology services and billing the patient or their insurance provider.

BRIEF DESCRIPTION OF THE DRAWINGS

FIG. 8a shows the center of gravity of the image and the average radius for determining coefficient of variance of the radius, and FIG. 8b shows the distances from the center of gravity used to determine radius aspect.

DETAILED DESCRIPTION

Figure 1:
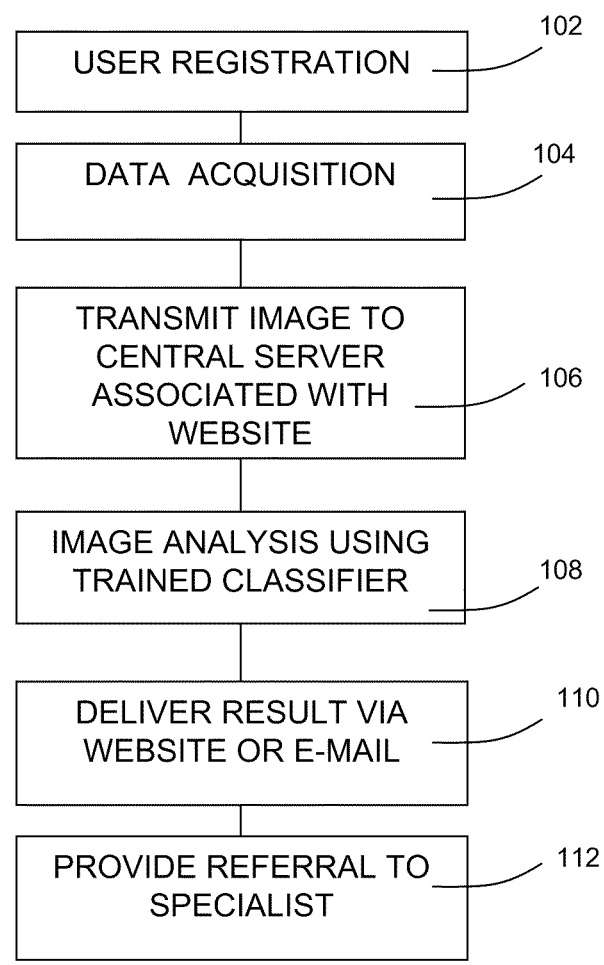
FIG. 1 is a flow diagram of an exemplary method according to the invention.

The present invention provides methods, systems and devices for discovering knowledge from data using learning machines. Particularly, the present invention is directed to methods, systems and devices for knowledge discovery from data using learning machines that are provided information regarding changes in biological systems. More particularly, the present invention comprises methods of use of such knowledge for diagnosing and prognosing changes in biological systems such as diseases. Additionally, the present invention comprises methods, compositions and devices for applying such knowledge to the testing and treating of individuals with changes in their individual biological systems.

As used herein, "biological data" means any data derived from measuring biological conditions of human, animals or other biological organisms including microorganisms, viruses, plants and other living organisms. The measurements may be made by any tests, assays or observations that are known to physicians, scientists, diagnosticians, or the like. Biological data may include, but is not limited to, clinical tests and observations, including medical images, physical and chemical measurements, genomic determinations, proteomic determinations, drug levels, hormonal and immunological tests, neurochemical or neurophysical measurements, mineral and vitamin level determinations, genetic and familial histories, and other determinations that may give insight into the state of the individual or individuals that are undergoing testing. Herein, the use of the term "data" is used interchangeably with "biological data".

While several examples of learning machines exist and advancements are expected in this field, the exemplary embodiments of the present invention focus on the support vector machine. As is known in the art, learning machines comprise algorithms that may be trained to generalize using data with known outcomes. Trained learning machine algorithms may then be applied to cases of unknown outcome for prediction. For example, a learning machine may be trained to recognize patterns in data, estimate regression in data or estimate probability density within data. Learning machines may be trained to solve a wide variety of problems as known to those of ordinary skill in the art. A trained learning machine may optionally be tested using test data to ensure that its output is validated within an acceptable margin of error. Once a learning machine is trained and tested, live data may be input therein. The live output of a learning machine comprises knowledge discovered from all of the training data as applied to the live data.

In a first exemplary embodiment, the present invention provides a system and method for diagnosing melanoma from images taken with a smart phone, such as the iPhone® (Apple, Inc.), RIM Blackberry®, Windows® Mobile, Google® Android, and similar mobile phones with PC-like functionality and cameras, and transmitted to a central server, e.g., by email or download to a website. The inventive method includes an approach in which the quality of the smart phone images could be improved by helping the user to take better pictures and crop the area of interest. In addition to providing the photographic image of the suspected melanoma, the user may be asked to provide information obtained from self examination, such as changes in size, shape, color, itching, or pictures of other less worrying moles. After classification of the image using a trained machine classifier, the result can be provided in an educational form to assist the patient in understanding the diagnosis and decide whether to consult a doctor.

FIG. 1 provides a high level flow diagram showing the modular components of the screening process using a smart phone with multi-media capability and Internet access according the present invention. In step 102, the person wishing to obtain a melanoma screening provides requested information by accessing a website linked to an image analysis server. In addition to identification or registration information, in step 104, the requested information may include a series of questions that will better enable the image analysis and classification process to evaluate the requester's risk of melanoma. The questions may include dimensional information, how long ago the suspect lesion was noticed, any changes, etc. If the requester is using a smart phone, he or she will be instructed to take a photograph of the suspected melanoma lesion using the built-in camera of the smart phone. Instructions may be provided to the requester to optimize the image by cropping or improving the lighting conditions. As an alternative to a smart phone, a digital camera may be used and the jpeg or other file format downloaded and saved on the smart phone or a personal computer or laptop. In step 106, the requester transmits the digital photograph to the central server by e-mail, or alternatively by downloading the image to a website associated with the server. An image analysis server that is programmed to execute pre-processing algorithms for extracting relevant features and a classifier that has been trained to distinguish between melanoma and other conditions is used to process the input image (step 108) to assign the suspected cancer to one of a small number of risk categories ranging from low to high, or to provide a probability which is considered a "risk score". In step 110, a report in the form of the risk score is transmitted to the smart phone or to the user's e-mail address, or is made available on-line with password protection. Examples of classifiers that may be appropriate for use in generating a risk score based on analysis of different features of interest within an image can be found in U.S. Pat. No. 6,658,395 of Barnhill and U.S. Pat. No. 6,996,549 of Zhang, et al., both of which are assigned to the assignee of the present invention, and both of which are incorporated herein by reference. The risk score may be accompanied by a table explaining the scoring levels, and additional information may be provided about melanoma. In a final step (112), the central server will search a database to provide the requester with referrals to a physician who specializes in treatment of skin cancers. The present invention is not intended to provide a definitive diagnosis or not of melanoma; it is merely intended to serve as a simple, low-cost preliminary screening tool to allow a person to obtain an advisory indication of whether he or she should seek a formal medical evaluation.

Figure 2:
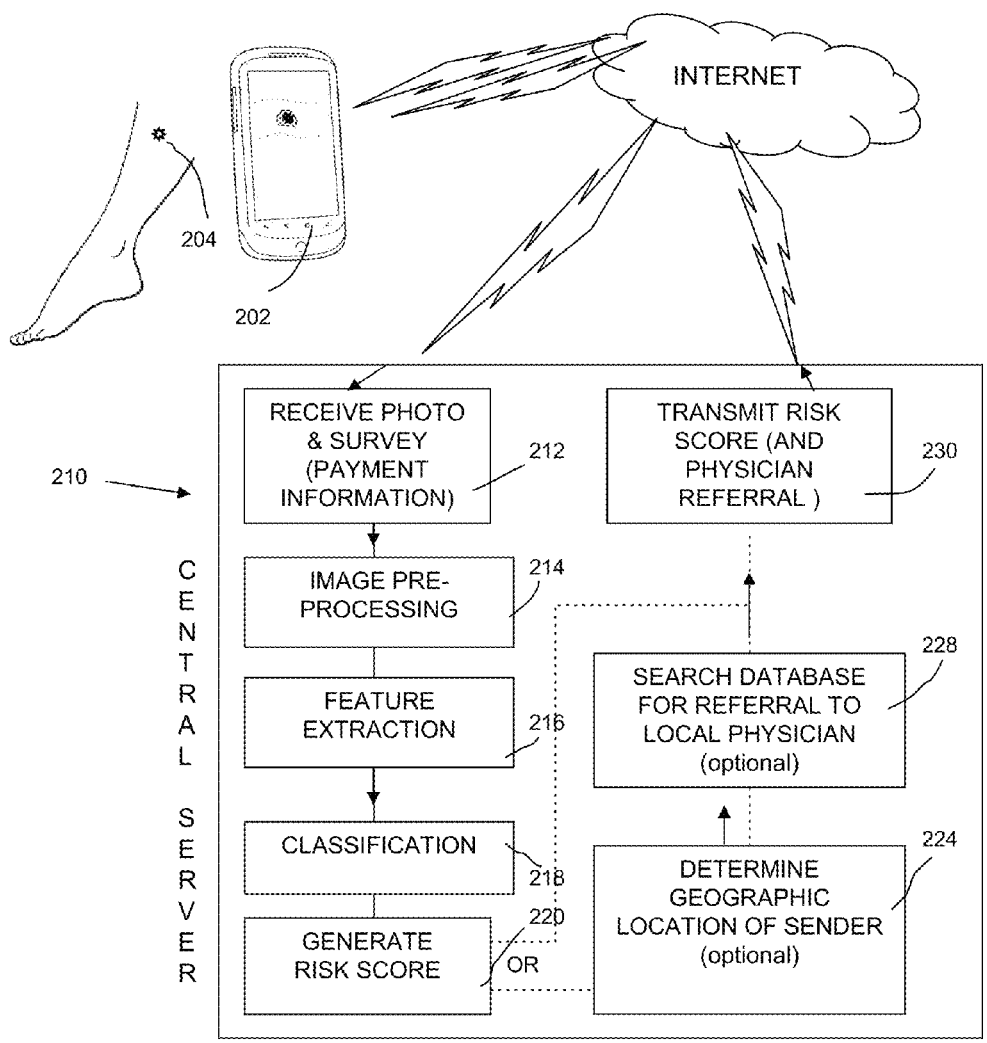
FIG. 2 is a functional block diagram of a network based system for providing melanoma screening.

FIG. 2 provides a high-level functional block diagram of the system and method for preliminary melanoma screening using a smart phone. The requester, in this example, a smart phone user, uses the camera function of the smart phone 202 to take a photograph of the suspected melanoma site 204 and selects the phone's e-mail function to transmit the photograph over the Internet 206 to the system's central server 210 along with identifying information, such as a user name or number. In a preferred embodiment, the user will be requested to respond to a number of survey questions that will assist in the classification. In one embodiment, for privacy purposes, the user's identity will not be utilized, but an account number or password may be assigned. If a payment is to be made for the analysis service, payment information, e.g., a credit card number, telephone number or other account information may be collected. The central server 210 receives the photograph, survey responses, and, if appropriate, the sender's identification and account information for payment. The central server may also request or automatically obtain the sender's geographic location. Location information may be obtained through the smart phone's GPS function, which may be obtained automatically if the sender has allowed unlimited access to their GPS information, or the sender may have granted permission to access their GPS function in response to a request sent by the central server. Alternatively, the sender's area code can be obtained from the caller ID, or the server can request that the sender enter their area or zip code.

The central server 210 may respond to the user with instructions to take the photograph at a shorter distance from the suspected lesion, to utilize additional lighting, e.g., a flash or to move closer to a light source, or to modify the original image by cropping it. These operations generally fall within step 302 (shown in FIG. 4) of the pre-processing block 214 even though they are not actually performed by the server. In one embodiment, the pre-processing block 214 may include an algorithm for screening spurious or "garbage" images that are not moles and could be either obviously bad data or a joke by a user who is playing with the screening service.

Figure 3:
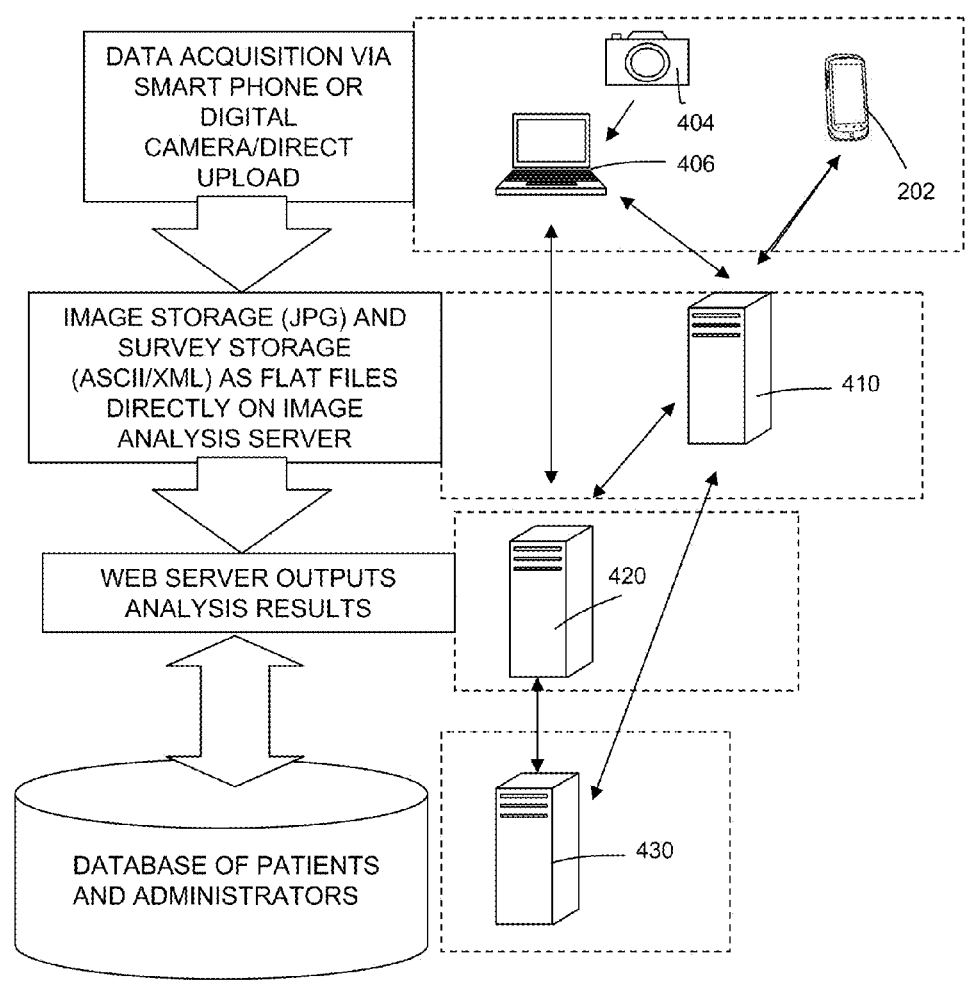
FIG. 3 is a block diagram of the basic architecture for a system according to the invention.

FIG. 3 provides a high-level block diagram of an embodiment of the modular system architecture for implementing the melanoma screening platform according to the present invention. In data acquisition module 402, the images may be captured either with a smart phone camera 202 or with a camera 404 and downloaded to a personal computer 406. (The camera 404 is preferably digital, but if not, the film images can be scanned using a color scanner and downloaded to the computer 406.) For each image capture device, an upload protocol will be implemented. The first protocol will be for a smart phone, e.g., an iPhone®, with dedicated image capture software and data transmission to the image analysis server 410. The second protocol will be for transmission by e-mail of an image captured using a standard mobile phone, digital camera or scanner. The third protocol will be an upload program on a website for images captured by a mobile phone, digital camera or scanner.

Answers to a short survey completed by the user may also be transmitted to the image analysis server 410 with the image and its meta data. The server may include programming to check continuously for incoming images. The images may be in a standard image format, such as jpeg, tiff or other format, while the answers to the survey may be an ASCII or XML format file. A user may be pre-registered, which will allow them to upload data via either a smart phone application or the website. The upload application, whether on the smart phone or on the website, will identify the user (patient), store the two files (image and text) using a specified file nomenclature. For example, the file names can be patientID_dattime.jpg and patientID_datetime.txt. In the case of a direct upload to the server, the user will be responsible for providing images of sufficient resolution, with good lighting and focus, following guidelines provided on the website. Guidelines may include suggested distance between the camera and the suspected melanoma and lighting conditions.

In the case of an upload via the smart phone application, the application software can transmit messages to the smart phone with guidance to the user such as indicating whether the lighting is sufficient, indicating whether the distance to the skin is appropriate to obtain proper focus, and helping the user crop the image. Suggestions may include finding an object to support the camera or smart phone to assist in holding the camera steady and parallel to the lesion. Ideally, the camera should be held 10-15 cm above the lesion. Instructions may include zooming in on the lesion using the touch screen slider to enlarge it to the maximum that fits in the screen, leaving a small border. A box or rectangle may be displayed on the screen to further assist the user.

The smart phone application may also transmit the location recorded with the GPS in the photos, assuming the "location services" function is turned on. Instead, if going through "Settings"—"General", obtaining the GPS information can be incorporated into the coding of the application. Some smart phones with built-in GPS receivers are able to encode location information directly in the EXIF (exchangable image file format) meta data associated with the transmitted image. All EXIF meta data will be transmitted to the central server, which can provide autofocus information, which may be used to determine image scale. In some smart phones, the EXIF data is automatically stripped away when the photos are e-mailed, so the application must include provisions to allow the EXIF data to be transmitted.

The following provides an example of EXIF meta data that may collected from an Apple iPhone for use in the melanoma screening application of the present invention:

| | |
|---|---|
| Filename: | [1 × 64 char] |
| FileModDate: | '24-Nov-2009 18:00:31' |
| FileSize: | 964263 |
| Format: | 'jpg' |
| FormatVersion: | '' |
| Width: | 1536 |
| Height: | 2048 |
| BitDepth: | 24 |
| Colortype: | 'truecolor' |
| FormatSignature: | '' |
| NumberofSamples: | 3 |
| CodingMethod: | 'Huffman' |

-continued

| | |
|---|---|
| CodingProcess: | 'Sequential' |
| Comment: | {[1 × 10 char]} |
| Make: | 'Apple' |
| Model: | 'iPhone 3GS' |
| Orientation: | 1 |
| XResolution: | 72 |
| YResolution: | 72 |
| ResolutionUnit: | 'Inch' |
| Software: | 'QuickTime 7.6.4' |
| DateTime: | '2009:11:24 18:00:31' |
| HostComputer: | 'Mac OS X 10.5.8' |
| YCbCrPositioning: | 'Centered' |
| DigitalCamera: | [1 × 1 struct] |
| GPSInfo: | [1 × 1 struct] |
| info.DigitalCamera | |
| ExposureTime: | 9.0334e−04 |
| FNumber: | 2.800 |
| ExposureProgram: | 'Normal program' |
| ISOSpeedRatings: | 70 |
| ExifVersion: | [4 × 1 double] |
| DateTimeOriginal: | '2009:11:24 13:54:11' |
| DateTimeDigitized: | '2009:11:24 13:54:11' |
| ShutterSpeedValue: | 10.1123 |
| ApertureValue: | 2.9709 |
| MeteringMode: | 'Average' |
| Flash: | [1 × 133 char] |
| FocalLength: | 3.8500 |
| ColorSpace: | 'sRGB' |
| SensingMethod: | 'One-chip color area sensor' |
| info.GPSInfo | |
| GPSLatitudeRef: | 'N' |
| GPSLattitude: | [3 × 1 double] |
| GPSLongitudeRef: | 'W' |
| GPS Longitude: | [3 × 1 double] |
| GPSAltitudeRef: | 0 |
| GPSAltitude: | 304 |

The upload program will also interact with the database server 430 to identify the user and notify the database server 430 of the upload of image(s) and survey responses. The patient and administrator database on database server 430 may be a mySQL database for holding the user database. The database server will be accessible to two types of users: patients and administrators. The user table may include basic demographic information: Name, Address, Email (which can serve as the user's login), password. Users may be registered with a unique ID which can be automatically generated. Patient user privileges on the database server 430 can include uploading images and accessing their own "My Lab" space on the website. Administrator user privileges may include patient user privileges plus access to the administrative backend to allow editing of website contents and management of the patient user database. Each patient/user will typically have a number of image records stored in the database with associated survey data and the corresponding image analysis result(s). The database server 430 must have scalable capacity. It need not physically be a separate server structure—it may be the same as the web server 420.

The transmitted images (jpeg or other standard image format) and survey data (ASCII or XML) may stored directly on the image analysis server 410 as flat files. As soon as the images and surveys are uploaded, they can be processed by image analysis server 410. The image analysis software may be implemented in Matlab® (Mathworks, Natick, Mass.), however, a faster platform may be preferred for performance reasons.

As will be readily apparent to those in the art, if the image analysis software is implemented in Matlab®, a computer server running Matlab® would be preferred in order to integrate the image analysis software with the rest of the platform. In the test system, the Causality Workbench, which is a web-based project for developing causal discovery algorithms supported by the National Science Foundation under Grant N0 ECCS-0725746, was used. To run the test software, an exemplary image analysis server may include the following features: a Microsoft® Windows® 2003 server with IIS, 2-4 Gbytes of RAM, 500 Gbytes of disk space, upgradable, to store images. The server configuration requirements may include: allow RSH, configure as web server, configure as ftp server, install mySQL and PHP, install Perl, install Matlab® with the Statistics, Image Processing and Optimization toolboxes (also from Mathworks). An alternative server would be a Linux Redhat Enterprise 5 Server with the Apache HTTP server software. The image analysis server 410 preferably includes storage for all images and surveys and interacts with the database server 430 and the web server 420, including notifying the database server 430 when the image analysis is completed.

The web server 420 will serve static pages with various types of information, for example, statistics on melanoma, as well as dynamic pages, which will include the analysis results and physician referral pages and/or links based on the user's geographical location information. Optionally, the web server 420 may also include advertisements for physicians or for skin care products such as sun screen and other protective skin treatments.

Figure 4:
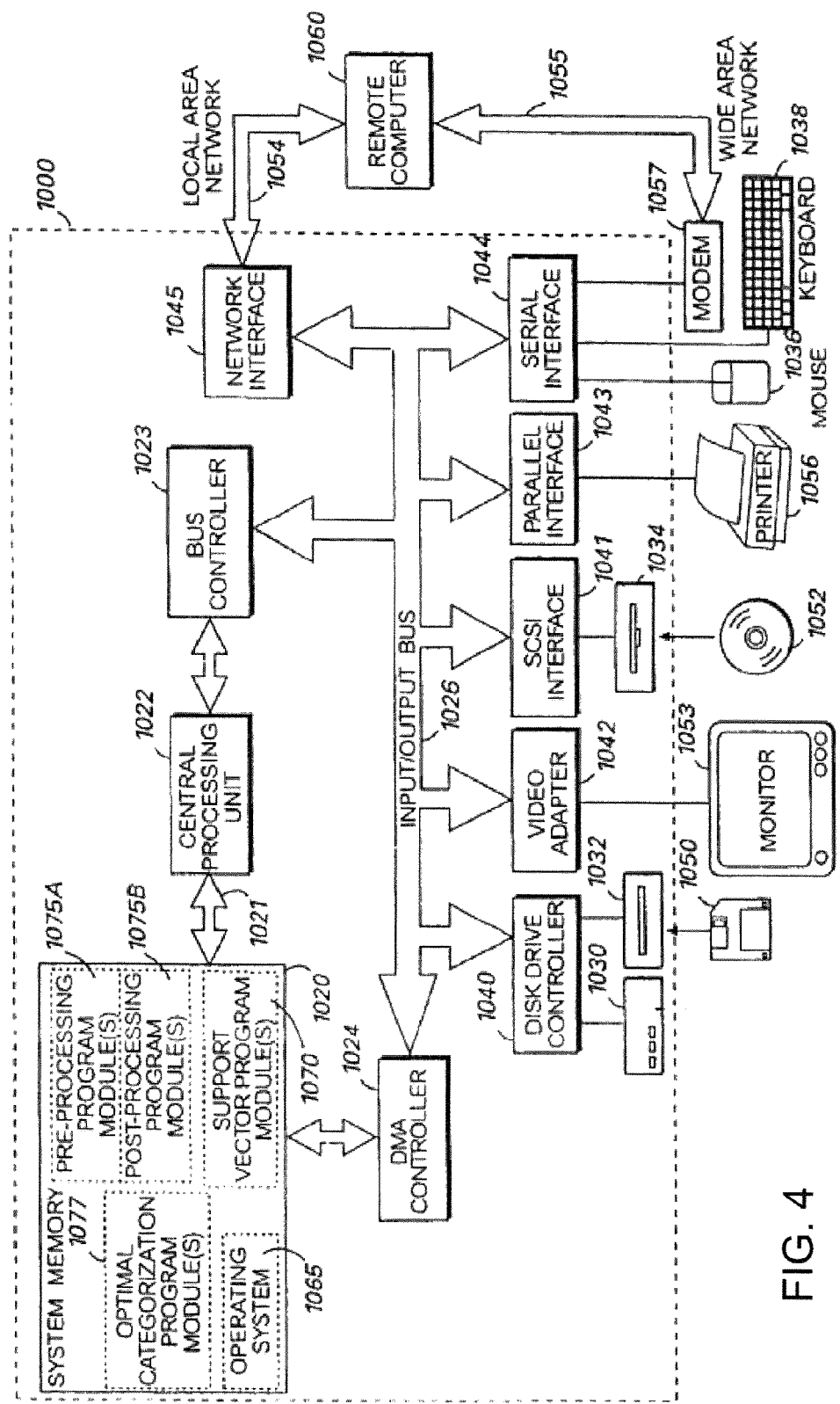
FIG. 4 is a functional block diagram of an exemplary operating environment for an embodiment of the present invention.

FIG. 4 and the following discussion are intended to provide a brief and general description of a suitable computing environment for implementing one aspect of the present invention. Although the system shown in FIG. 4 is a conventional personal computer 1000, those skilled in the art will recognize that the invention also may be implemented using other types of computer system configurations. The computer 1000 includes a central processing unit 1022, a system memory 1020, and an Input/Output ("I/O") bus 1026. A system bus 1021 couples the central processing unit 1022 to the system memory 1020. A bus controller 1023 controls the flow of data on the I/O bus 1026 and between the central processing unit 1022 and a variety of internal and external I/O devices. The I/O devices connected to the I/O bus 1026 may have direct access to the system memory 1020 using a Direct Memory Access ("DMA") controller 1024.

The I/O devices are connected to the I/O bus 1026 via a set of device interfaces. The device interfaces may include both hardware components and software components. For instance, a hard disk drive 1030 and a floppy disk drive 1032 for reading or writing removable media 1050 may be connected to the I/O bus 1026 through disk drive controllers 1040. An optical disk drive 1034 for reading or writing optical media 1052 may be connected to the I/O bus 1026 using a Small Computer System Interface ("SCSI") 1041. Alternatively, an IDE (ATAPI) or EIDE interface may be associated with an optical drive such as a may be the case with a CD-ROM drive. The drives and their associated computer-readable media provide nonvolatile storage for the computer 1000. In addition to the computer-readable media described above, other types of computer-readable media may also be used, such as ZIP drives or removable media such as flash drives or the like.

A display device 1053, such as a monitor, is connected to the I/O bus 1026 via another interface, such as a video adapter 1042. A parallel interface 1043 connects synchronous peripheral devices, such as a laser printer 1056, to the I/O bus 1026. A serial interface 1044 connects communication devices to the I/O bus 1026. A user may enter commands and information into the computer 1000 via the serial interface 1044 or by using an input device, such as a keyboard 1038, a mouse 1036 or a modem 1057. Other peripheral devices (not shown) may also be connected to the computer 1000, such as audio input/output devices or image capture devices.

A number of program modules may be stored on the drives and in the system memory 1020. The system memory 1020 can include both Random Access Memory ("RAM") and Read Only Memory ("ROM"). The program modules control how the computer 1000 functions and interacts with the user, with I/O devices or with other computers. Program modules include routines, operating systems 1065, application programs, data structures, and other software or firmware components. In an illustrative embodiment, the present invention may comprise one or more pre-processing program modules 1075A, one or more post-processing program modules 1075B, and/or one or more optimal categorization program modules 1077 and one or more SVM program modules 1070 stored on the drives or in the system memory 1020 of the computer 1000. Specifically, pre-processing program modules 1075A, post-processing program modules 1075B, together with the SVM program modules 1070 may comprise computer-executable instructions for pre-processing data and post-processing output from a learning machine and implementing the learning algorithm according to the exemplary methods described herein. Furthermore, optimal categorization program modules 1077 may comprise computer-executable instructions for optimally categorizing a data set.

The computer 1000 may operate in a networked environment using logical connections to one or more remote computers, such as remote computer 1060. The remote computer 1060 may be a server, a router, a peer device or other common network node, and typically includes many or all of the elements described in connection with the computer 1000. In a networked environment, program modules and data may be stored on the remote computer 1060. The logical connections depicted in FIG. 4 include a local area network ("LAN") 1054 and a wide area network ("WAN") 1055. In a LAN environment, a network interface 1045, such as an Ethernet adapter card, can be used to connect the computer 1000 to the remote computer 1060. In a WAN environment, the computer 1000 may use a telecommunications device, such as a modem 1057, to establish a connection. It will be appreciated that the network connections shown are illustrative and other devices of establishing a communications link between the computers may be used.

Figure 5:
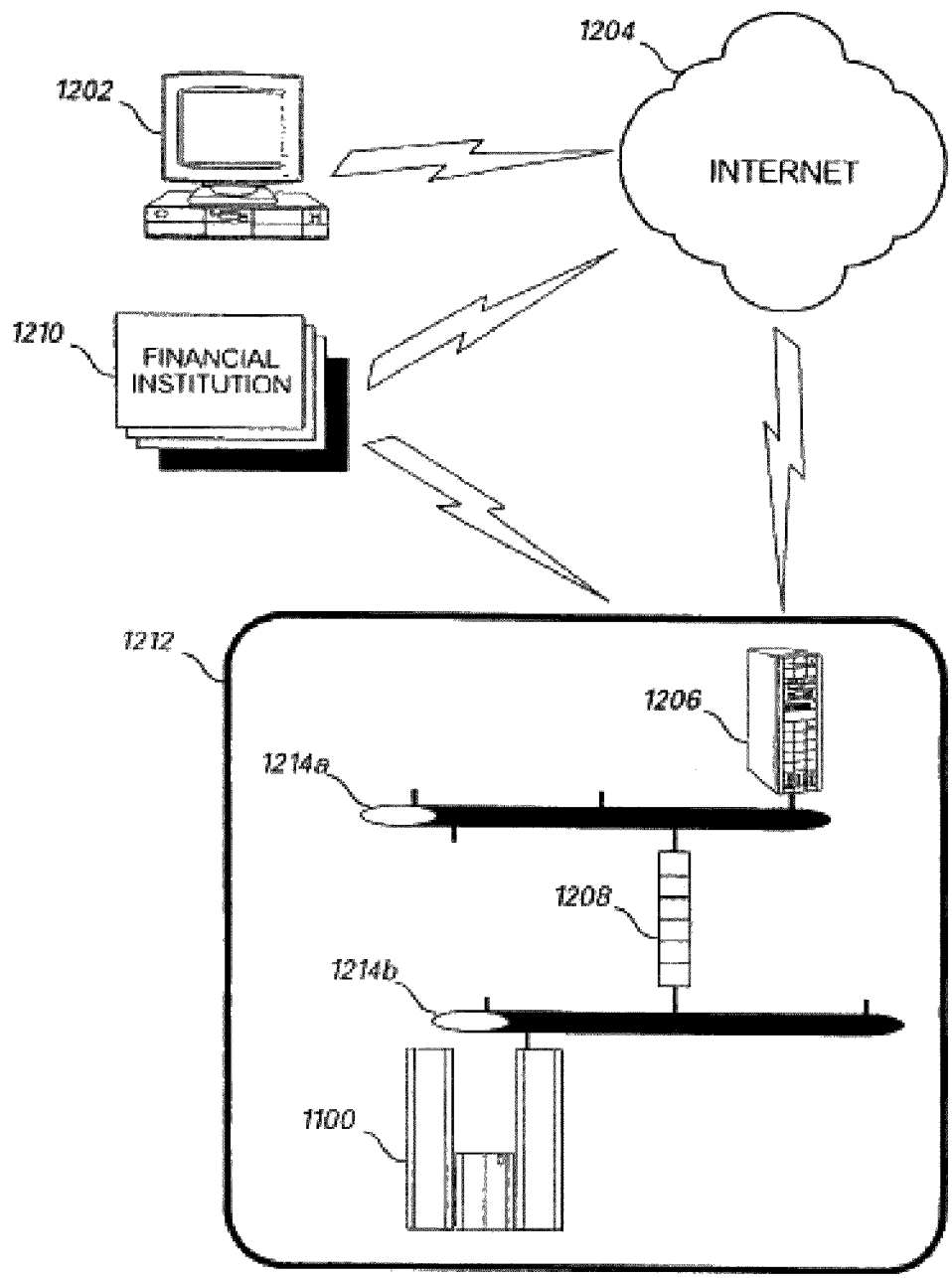
FIG. 5 is a functional block diagram of an exemplary network operating environment for implementation of the present invention.

FIG. 5 is a functional block diagram illustrating an exemplary network operating environment for implementation of the present invention. In the exemplary network operating environment, a remote user 1202 or other entity may transmit data via a distributed computer network, such as the Internet 1204, to a service provider 1212, e.g., a website host, who provides analysis services as described above. Those skilled in the art should appreciate that the customer 1202 may transmit data from any type of computer, laboratory instrument or multi-media device, including a smart phone, with network capability that includes or is in communication a distributed network. The data transmitted from the remote user 1202 may be training data, test data and/or live data to be processed by a learning machine. In the preferred embodiment, the classifier is pre-trained so that the remote user sends live data. The data transmitted by the customer is received at the central server 1206, which may transmit the data to one or more learning machines via an internal network 1214*a-b*. As previously described, learning machines may comprise SVMs, neural networks, random forests, Bayesian classifiers, or other learning machines or combinations thereof. Preferably, the web server 1206 is isolated from the learning machine(s) by way of a firewall 1208 or other security system. The service provider 1212 may also be in communication with one or more financial institutions 1210, via the Internet 1204 or any dedicated or on-demand communications link. The web server 1206 or other communications device may handle communications with the one or more financial institutions. The financial institution(s) may comprise banks, Internet banks, clearing houses, credit or debit card companies, or the like. Where the remote user is using a smart phone, the financial institution may also be a wireless service provider.

In operation, the service provider may offer learning machine processing services via a web-site hosted at the web-server 1206 or another server in communication with the web-server 1206. A customer 1202 may transmit data to the web server 1206 to be processed by a learning machine. The customer 1202 may also transmit identification information, such as a username, a password and/or a financial account identifier, to the web-server. In response to receiving the data and the identification information, the web server 1206 may electronically withdraw a pre-determined amount of funds from a financial account maintained or authorized by the customer 1202 at a financial institution 1210. In addition, the web server may transmit the customer's data to the classifier 1100. When the classifier 1100 has completed processing of the data and post-processing of the output, the post-processed output is returned to the web-server 1206. As previously described, the output from a learning machine may be post-processed in order to generate a single-valued or multi-valued, computationally derived alpha-numerical classifier, for human or automated interpretation. The web server 1206 may then ensure that payment from the customer has been secured before the post-processed output is transmitted back to the customer 1202 via the Internet 1204.

An exemplary implementation of the website may include five pages that hold the main functionalities: Welcome (which may serve as the index page); Facts: Statistics and Background Information on Melanoma; Upload Photo: upload page; MyLab: where the analysis results can be retrieved. Additional pages may include a Terms and conditions page to advise the user that the application is for educational purposes only and is not intended to serve as a medical diagnostic tool and requesting acknowledgement that the user has read and understood the terms and conditions. The Statistics and Background information page may include introductory information about melanoma and why such an application may be beneficial to the user.

Preferably, the MyLab page will be confidential to each patient user; Referrals: for directing patient users to medical professionals, e.g., physicians, dermatologists. A navigation bar may be provided on each page for accessing the other pages. The web server 420 should have scalable bandwidth. It should be noted that while the web server 420 and database server 430 are illustrated as physically separate servers, they may be combined within a single server.

The user's identification and geographical location may be stored on the database server 430 in the database of patients (users) and system administrators. Also stored on server 430 will be information about referral physicians and other relevant data. All three servers will be accessible to administrators. A web-based administration interface will allow the administrators to perform the most basic tasks, which may include changing content in the web pages, deletion of users, or database entries.

The exemplary architecture described above combines a fully integrated service with a modular design that allows expansion and development of different modules, independent of the other modules. The modular design will also permit implementation and maintenance of different modules/servers by different entities. For example, the database server may be a combination of different servers in which one server holds a referral database that is maintained by a for-fee referral service that contracts with physicians and receives compensation for each referral.

Figure 6:
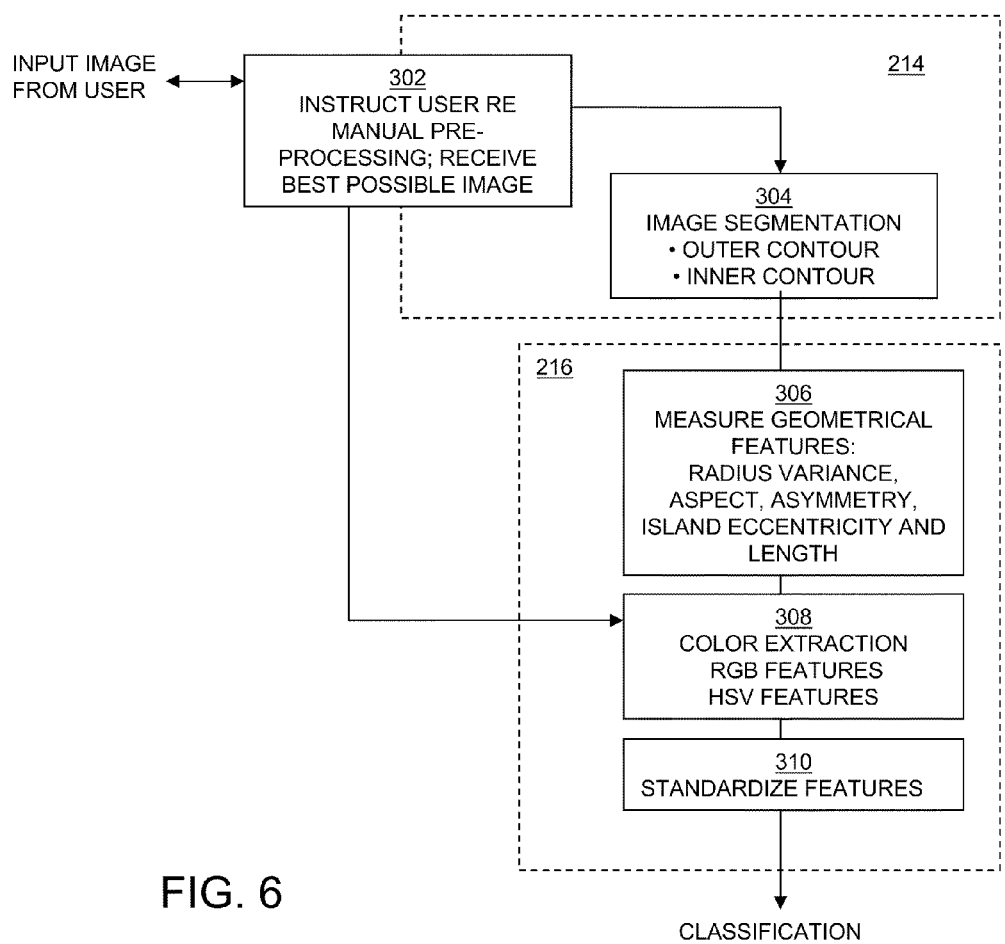
FIG. 6 is a block diagram showing additional details of an exemplary implementation of the image preprocessing and feature selection components of the system.
Figure 7:
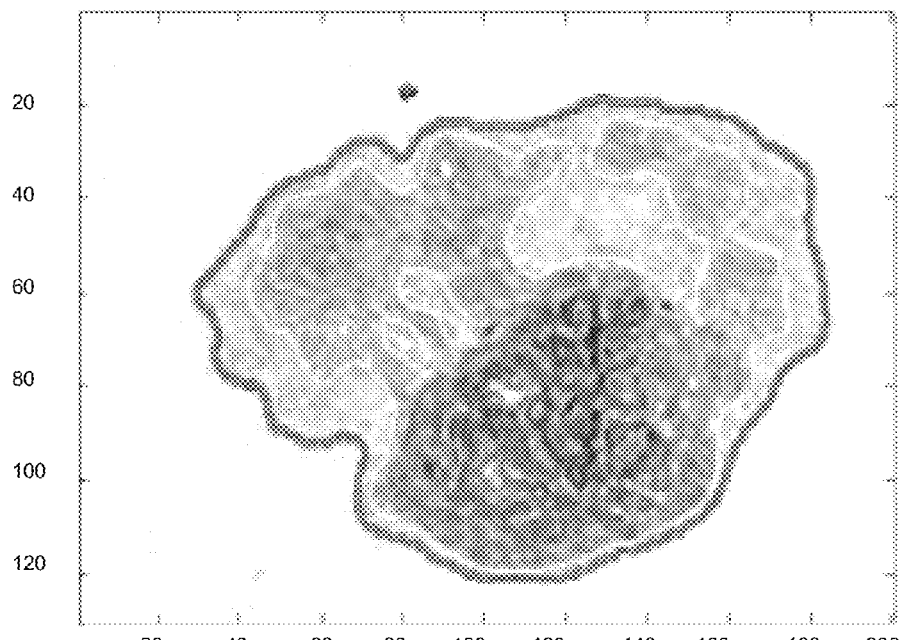
FIG. 7 is a digital image of an exemplary suspected melanoma showing the outer and inner contours extracted by the segmentation algorithm.

FIG. 6 illustrates the various components of the image pre-processing and feature selection operations. After manual pre-processing by the user (step 302), the best possible image received by the image analysis server for further processing. The next stage of pre-processing block 214 includes execution of a segmentation algorithm (step 304) which is applied to the original image to isolate the area of interest from the background. In biomedical image segmentation, most techniques can be categorized into three classes: (1) characteristic feature thresholding or clustering, (2) edge detection, and (3) region extraction tasks such as measurements and registration. In the exemplary embodiment, edge detection is used to identify the outer contours of the suspected lesion, as shown in FIG. 7. It will be readily apparent to those in the art that other segmentation methods may be used. The image analysis server pre-processes the image by converting it into a gray scale image, smoothing and equalizing. This step facilitates extraction of the contour by setting a threshold on a histogram of the gray scale values. Different gray scale values may also be used to extract inner contours within the lesion.

Also included in pre-processing bloc 214, but not shown in FIG. 6 is the identification and screening of junk images. The ABC features used for the melanoma recognizer rely on the identification of the mole outline, so if an image does not include a mole, the system will return senseless results. To discriminate between "garbage" images and actual skin disease images, a data representation that does not rely on mole segmentation may be used. In one embodiment, a new feature set may include two types of features: geometrical features assessing the symmetry of the image and color spectrum features. Additional features may include shape spectral features.

Figure 19A:
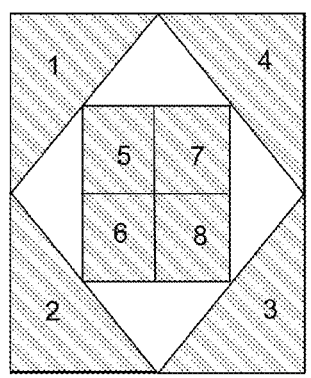
FIGS. 19a-19c are exemplary geometric constructs for feature extraction for use in screening out garbage images.

A set of geometrical constructs may be used for the garbage image screening. To extract the color spectrum features, several areas in the image are evaluated using a grid such as shown in FIG. 19a, where eight areas are shown. In each area, the three median RGB and the three median HSV values are calculated along with their standard deviation. For each of these twelve features, the minimum, maximum and average value in the outer sectors $\{1, 2, 3, 4\}$ and in the inner sectors $\{5, 6, 7, 8\}$ were computed, resulting in 12×6=72 color spectrum features.

Figure 19B:
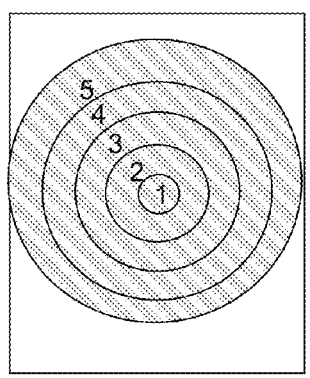

To extract circular symmetry features, the gray level image obtained by averaging the RGB values was used and computed. The standard deviation of the gray levels in five concentric rings shown in FIG. 19b was then calculated. The minimum, maximum, and mean values of these five coefficients were used to evaluate three symmetry features.

Figure 19C:
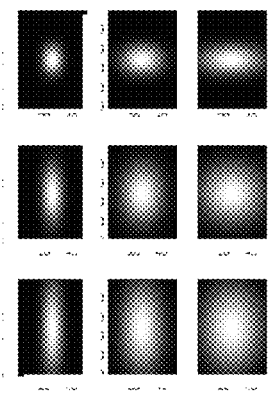

In a third step, the presence of a blob was assessed by correlating the image with nine masks featuring a Gaussian gray-level shape, as shown in FIG. 19c. The minimum, maximum, and mean value of the nine quantities were taken to produce three "blob" features.

Altogether, the data representation consisted of 78 features. The minimum, maximum, and average are quite correlated. To assess the data representation, we performed 5-fold cross-validation experiments with 4 classifiers: Naïve Bayes, Linear kernel classifier, Second degree kernel classifier and Radial basis kernel (RBF) Gaussian classifier. A kernel ridge regression classifier, analogous to an SVM, was used. The hyper-parameters were adjusted using the virtual-leave-one-out method. The results are summarized in Table 1 below. A dramatic performance improvement was obtained by adding the standard deviation features. Additional improvement was obtained with the geometric features (blob and symmetry).

TABLE 1

| Features | Classifier | | | |
|---|---|---|---|---|
| | Naïve Bayes | Linear kernel | Poly2 kernel | RBF kernel |
| Color = RGB + HSV | 0.70 | 0.92 | 0.72 | 0.90 |
| AllCol = RGB + HSV + Std | 0.95 | 0.97 | 0.77 | 0.98 |
| AllCol + Blob + Symmetry | 0.98 | 0.99 | 0.84 | 0.99 |

Although the RBF kernel gives a slightly better performance than the linear kernel (0.9924 vs. 0.9915), the difference is not significant, and the linear kernel was selected.

For verification, an experiment was performed by splitting the data into a training and a test set in which the training images were from different image classes as those of the test set. The resulting area under the curve (AUC) on test data was 0.9927.

In an effort to analyze the efficacy of the features extracted, classifiers were built with subsets of features: "Blob" (the three "blob" features), "Sym" (the three "symmetry" features), "Out" (the color features for the four outer zones), and "In" (the color features for the 4 inner zones):

| | |
|---|---|
| Blob | AUC = 0.84 |
| Sym | AUC = 0.96 |
| Out | AUC = 0.95 |
| In | AUC = 0.98 |

Hence, it appears that the color at the center of the image is the most important feature and may alone be sufficient for classification of garbage images.

Figure 8A:
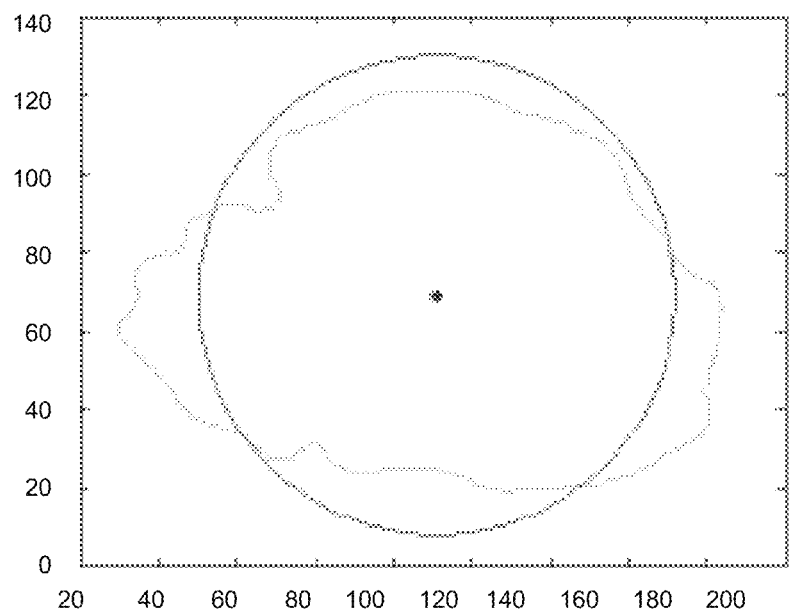
FIGS. 8a and 8b are plots used for measurement of the geometrical features of the suspected melanoma, where
Figure 8B:
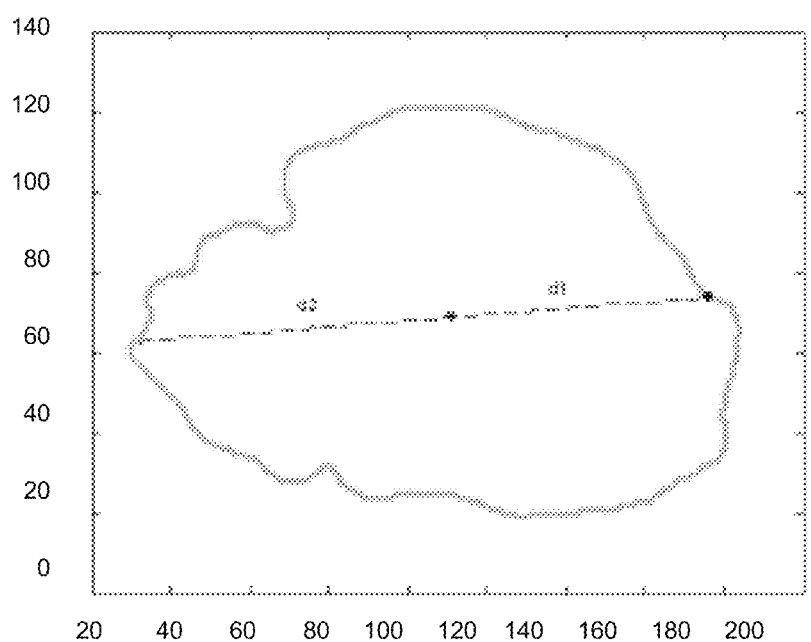

Referring again to FIG. 6, within the feature extraction block 216, step 306 includes using the outer contour to extract geometrical features by first identifying the center of gravity, or centroid, of the image and determining the average radius. (See FIG. 8a.) Next, the difference in distance from the center or gravity to opposite points on the contour is determined. The coefficient of variance of the radius ("radius_cv") is determined by calculating the standard deviation of the distance of a contour point to the center of gravity minus radius, divided by the mean radius. The mean radius (radius_mean) may be determined from the image if the user took the photograph with some form of dimensional reference, such as a ruler or a coin with known dimensions, or the value may also be obtained from the user-entered responses to the survey questions if they have provided the dimensions of the suspected melanoma. Alternatively, the diameter may be calculated using autofocus information contained within the EXIF meta data, if available. The radius aspect is the ratio of the minimum radius to the maximum radius. Asymmetry is measured using the distances between opposite points on the contour and the center of gravity (d1 and d2 in FIG. 8b). The average square difference between d1 and d2 is computed for all contour points, then the square root is taken and divided by the mean radius to normalize.

Additional geometrical features may be extracted using the inner contours, which are referred to as "islands". The eccentricity of the first island ("island1_eccentricity") is determined by measuring the distance between the center of gravity of the innermost contour and that of the outer contour, normalized by the mean radius. The island2_eccentricity is the distance between the center of gravity of the second most inner contour and that of the outer contour, again normalized by the mean radius. The contour length, "island1_clength", is the innermost contour normalized by the mean radius, and the island2_clength is the second most inner contour normalized by the mean radius.

In step 308, color features are computed using the original, unpreprocessed image, but with the contours defined in the preceding process (step 304) superimposed over the original image. Two sets of color features are used: the original RGB (red-blue-green) and the HSV (hue-saturation-value), providing a total of six channels. In typical RGB images, each color channel is coded on 8 bits for a total of 24 bits. These values are converted to HSV using methods that are well known in the art.

Figure 9A:
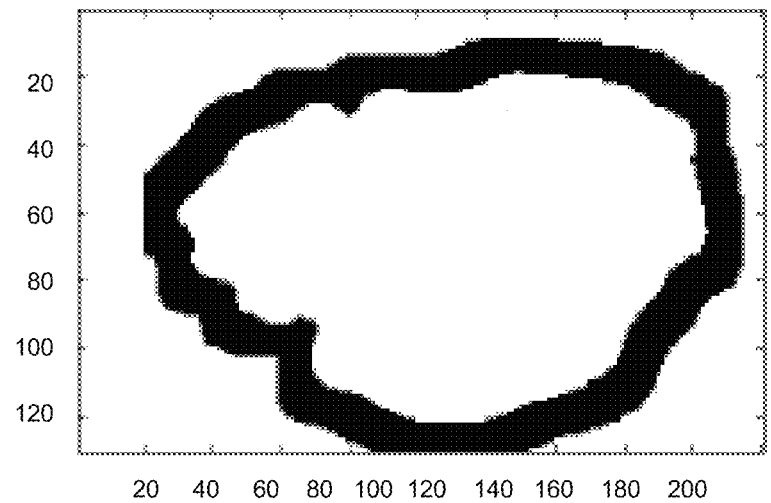
FIGS. 9a and 9b show the outer and inner contours, respectively, for comparison of color within and outside the contour.
Figure 9B:
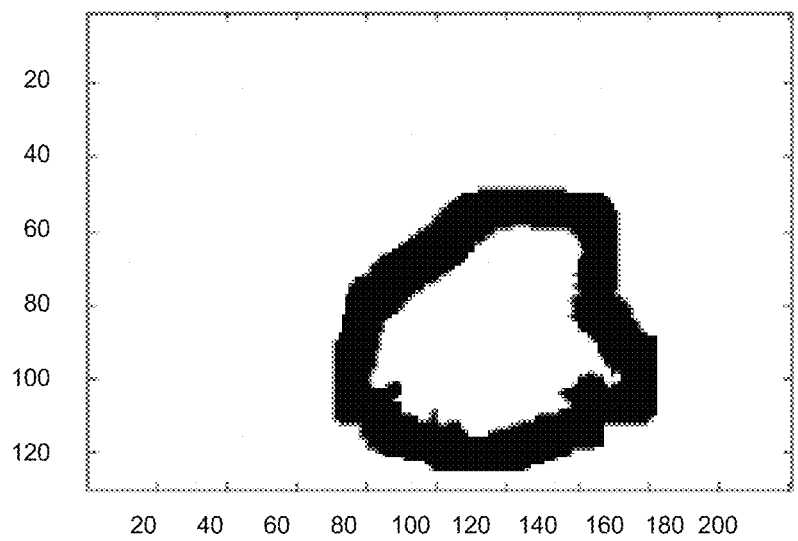

For each channel, RGB or HSV, the median value is computed within the contour and around the contour for both the outer and innermost contours using the narrow surrounding bands illustrated in FIGS. 9a and 9b for outer and inner contours, respectively. A color feature in a given channel, except for hue, is defined as the relative difference between the inner and outer values:

Color_feat=2·(outer_value−inner_value)/(outer_value+inner_value).

Hue($H$)=sin 2π(inner_value).

The above computations produce twelve color features:
color_R, color_G, color_B, color_H, color_S, color_V, and
color_island_R, color_island_G, color_island_B, color_island_H, color_island_S, and color_island_V.

In step 310, each of the features is standardized by subtracting the mean of all values of that feature and dividing the result by the standard deviation prior to loading into a feature matrix for classification.

Figure 10:
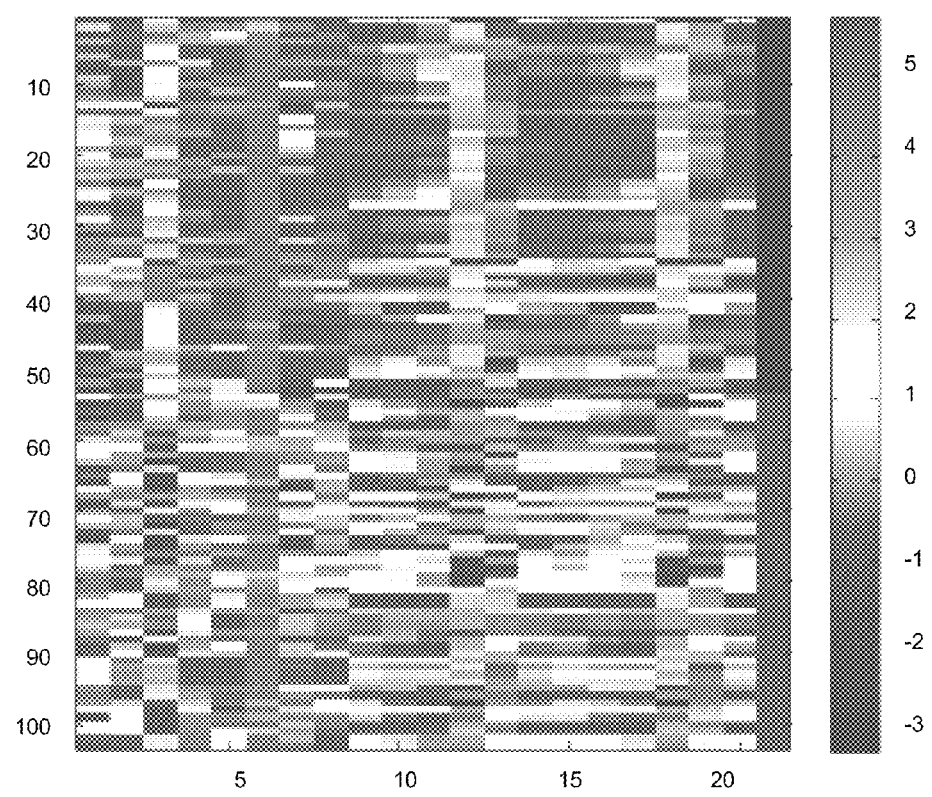
FIG. 10 is a gray scale feature matrix of an image dataset based on 20 features in which the upper half corresponds to controls and the lower half corresponds to malignant melanoma.

The classifiers used in step 218 for analysis of the user-provided image and data are pre-trained, i.e., trained and tested, using one or more image datasets having known outcomes. The feature matrix shown in FIG. 10 represents a training dataset with 103 cases of which 50 were images of malignant melanoma and 53 were controls including atypical nevi (27), atypical nevi demoscopy (7), congenital nevi (5), blue nevi (3), halo nevi (4), lentigo (6), and spitz nevus (1). Table 2 lists the features in the order shown (from left to right) in the x-axis of the feature matrix in FIG. 10.

TABLE 2

| FEATURE |
|---|
| radius_mean |
| radius_cv |
| radius_aspect |
| asymmetry |
| island1_eccentricity |
| island2_eccentricity |
| island1_length |
| island2_length |
| color_R |
| color_G |
| color_B |
| color_H |
| color_S |
| color_V |
| color_island_R |
| color_island_G |
| color_island_B |
| color_island_H |
| color_island_S |
| color_island_V |

The y-axis represents the 103 data samples, with the 53 controls at the top (#51-103) and 50 malignant samples (#1-50) at the bottom. The right hand column of the table indicates the class (control vs. malignant).

An ensemble of classifiers was trained using the features extracted from the image, with one classifier trained on each of the feature types A, B, C and D. As is known in the art, an ensemble of classifiers is a set of classifiers whose individual decisions are combined in some way to classify new examples. An ensemble may, but not necessarily, consist of a set of different classifier types. Table 3 lists the features that fall within the 4 feature types:

TABLE 3

| Feature Type | Features |
| --- | --- |
| A (Asymmetry) | radius_aspect, asymmetry, island1_eccentricity, island2_eccentricity |
| B (Border) | radius_cv, island1_length, island2_length |
| C (Color) | color_R, color_G, color_B; color_H, color_S, color_V, color_R, color_island_G, color_island_B; color_island_H, color_island_S, color_island_V, |
| D (Diameter) | radius_mean |

Each classifier of the ensemble uses standardized features, in which the mean of the features was subtracted and the result was divided by the standard deviation. The normalization coefficients are computed on training data and the same values are applied to the test data.

In a first embodiment, each classifier in the ensemble is a support vector machine classifier, with a separate kernel (trained and tested) used for each of the feature types. In an exemplary embodiment, a radial basis function (RBF) or Gaussian kernel is used. A linear SVM may also be used. In another embodiment, a univariate, Gaussian classifier may be used, however, other learning machine classifiers that are known in the art that may be used, including random forests, decision trees, neural networks and others, as well as combinations of different types of classifiers. The output of each classifier may be postprocessed with linear logistic regression to obtain a mapping of outputs to probabilities.

Figure 13:
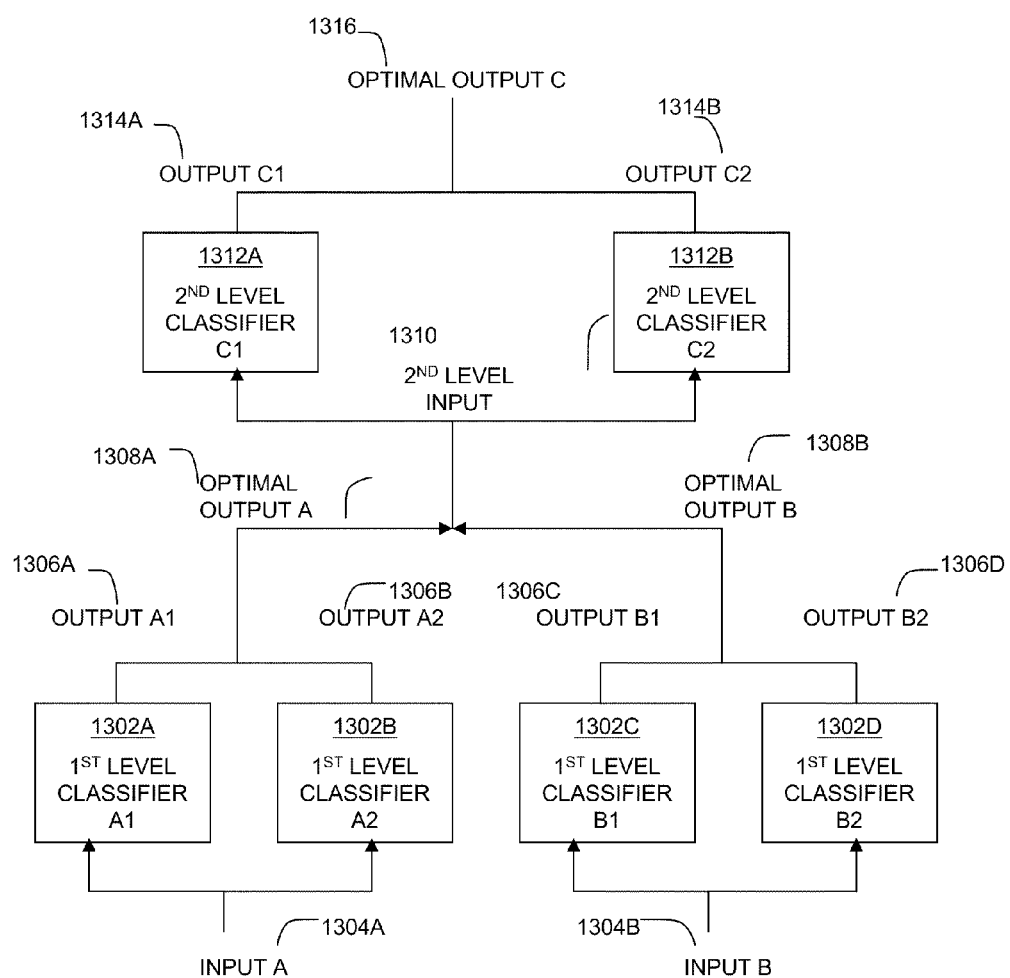
FIG. 13 is a functional block diagram of a hierarchical or ensemble classifier system.

FIG. 13 illustrates a basic example of a two level hierarchical system of classifiers, i.e., an ensemble of multiple classifiers that produces a final, integrated classification using a combination of input data types that are relevant to the knowledge to be discovered with base classifiers that process the different input data types for input into a second-level, integrating or stacking classifier.

As shown, one or more first-level, or base, classifiers 1302A and 1302B may be trained and tested to process a first type of input data 1304A, for example, mammography data, pertaining to a sample of medical patients. One or more of these classifiers may comprise a distinct kernel. Another one or more additional first-level classifiers 1302C and 1302D may be trained and tested to process a second type of data 1304B, for example, genomic data, for the same or a different sample of medical patients. Again one or more of the additional classifiers may comprise a distinct kernel. The output from each of the base classifiers may be compared with each other (i.e., output A1 (1306A) compared with output A2 (1306B); output B1 (1306C) compared with output B2 (1306D) in order to determine optimal outputs (1308A and 1308B). Then, the optimal outputs from the two types of base classifiers 1308A and 1308B may be combined to form a new multi-dimensional input data set 1310, which in this example relates to combined mammography and genomic data. The new data set may then be processed by one or more appropriately trained and tested second-level, or stacking, classifiers 1312A and 1312B. The resulting outputs 1314A and 1314B from the second-level classifiers 1312A and 1312B may be compared to determine an optimal output 1316. The optimal output 1316 may identify causal relationships between the mammography and genomic data points. As should be apparent to those of ordinary skill in the art, the contemplated hierarchy of learning machines may have applications in any field or industry in which analysis of data by a learning machine is desired.

The hierarchical processing of multiple data sets using multiple classifiers may be used as a method for pre-processing or post-processing data that is to be input to or output from still other learning machines. In addition, pre-processing or post-processing of data may be performed to the input data and/or output of the above-described hierarchical architecture of learning machines.

Figure 14:
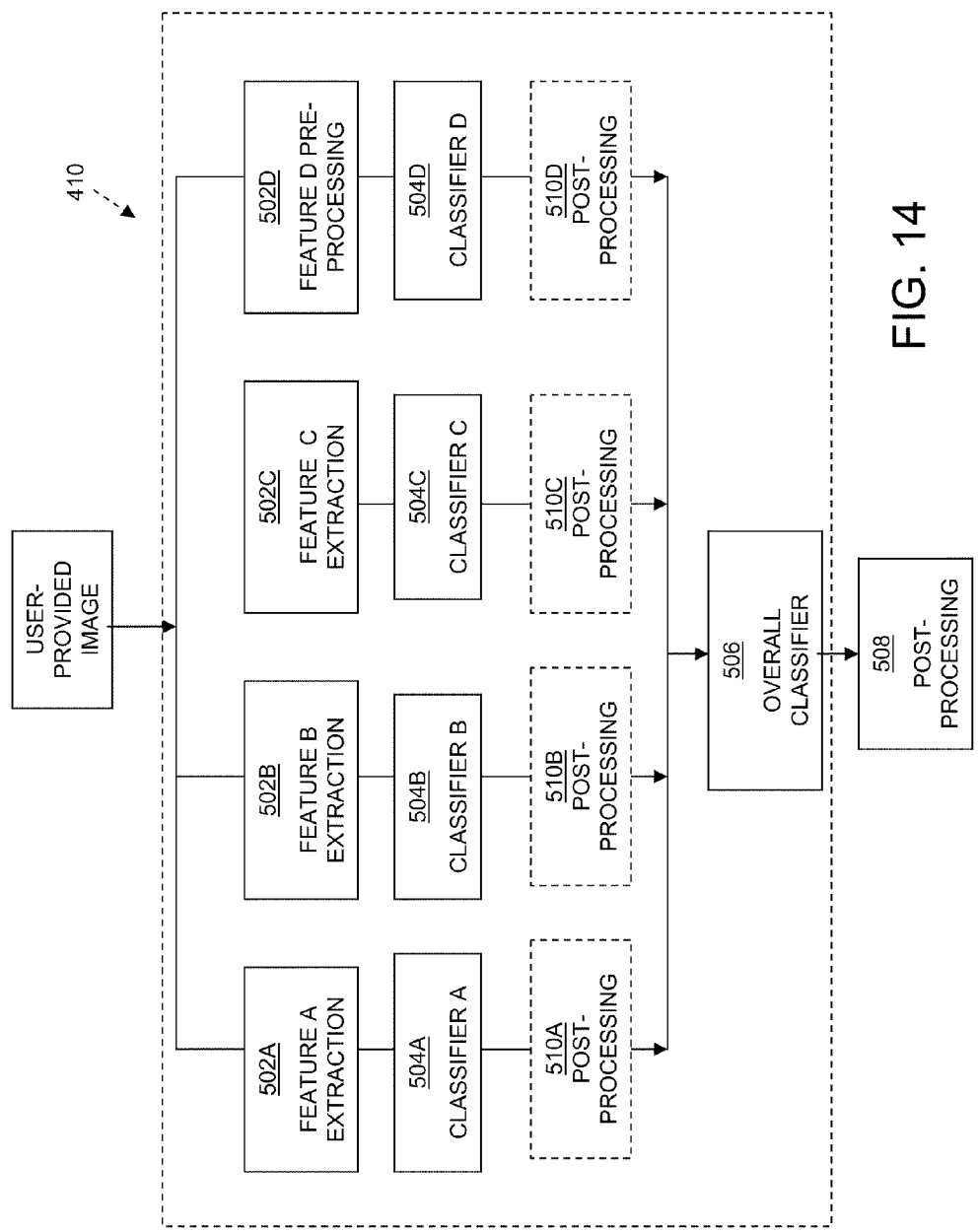
FIG. 14 is a functional block diagram of a multilevel classifier system for remote melanoma screening according to the present invention.

FIG. 14 illustrates an ensemble or hierarchical approach applied to image analysis of a user-provided image 500. The image analysis server 410 receives the downloaded image and performs the pre-processing steps 502A-502D needed to extract the ABCD features. Each extracted feature is separately processed using a trained base classifier 504A-504D, respectively, that has been optimized for classification of the corresponding ABCD feature, to generate an output that identifies whether the characteristics of the features extracted from the image correspond to a diagnosis of melanoma. The results of the classification of each of classifiers 504A-504D are combined to create the ensemble by overall classifier 506, generating a single result which is output for further processing. The overall classifier 506 may be a trained learning machine, such as a second support vector machine, or may simply be a weighted combination of the results of the individual classifiers 504A-D. The output of classifier 506 will typically be post-processed by the web server in step 508 to generate a result that is meaningful to the user. In the preferred embodiment, the result that is provided to the sender/user is a risk score or probability, along with graphics and information that can assist in interpretation of the score. In an optional step 510A-510D, the outputs of the individual classifiers 504A-D can be post-processed to generate a risk score or probability based on the corresponding A, B, C or D feature, which can also be provided to the sender/user with the overall risk score.

In an exemplary embodiment, the overall classifier 506 operated by voting of the different classifiers 504A-D, with each individual classifier being given a weight of 1. The resulting vote was postprocessed (step 508) with logistic regression to provide a probability value.

The following provides a listing of the CLOP code for the training and testing of the exemplary classifier. "CLOP" stands for Challenge Learning Object Package, which is incorporated herein by reference. It is an object-oriented Matlab® machine learning package and is based on the Spider developed at the Max Planck Institute for Biological Cybernetics.

```
DD=data (X,Y)
A=[3 4 5 6]
B=[2 7 8]
C=9:20
D=1
model_A=chain({standardize, fixed_fs(A), naive,klogistic});
model_B=chain({standardize, fixed_fs(B), naive,klogistic});
model_C=chain({standardize, fixed_fs(C), naive,klogistic});
```

```
model_D=chain({standardize, fixed_fs(D), naive,klogis-
tic});
    [d,m]=train(cv(model, {'folds=10', repeats=10'}), DD)
roc(d);
    [a, sa]=auc(d);
    [b,sb]=ber(d);
    fprintf('AUC=% 5.3f+−5.3f, BER=% 5.3f+−% 5.3f/n', a,
sa, b, sb);
```

Cross-validation (10×10-fold) produced the following results:

(AUC=area under ROC curve; BER=balanced error rate) AUC=0.910±0.010, BER=0.155±0.011.

Figure 11:
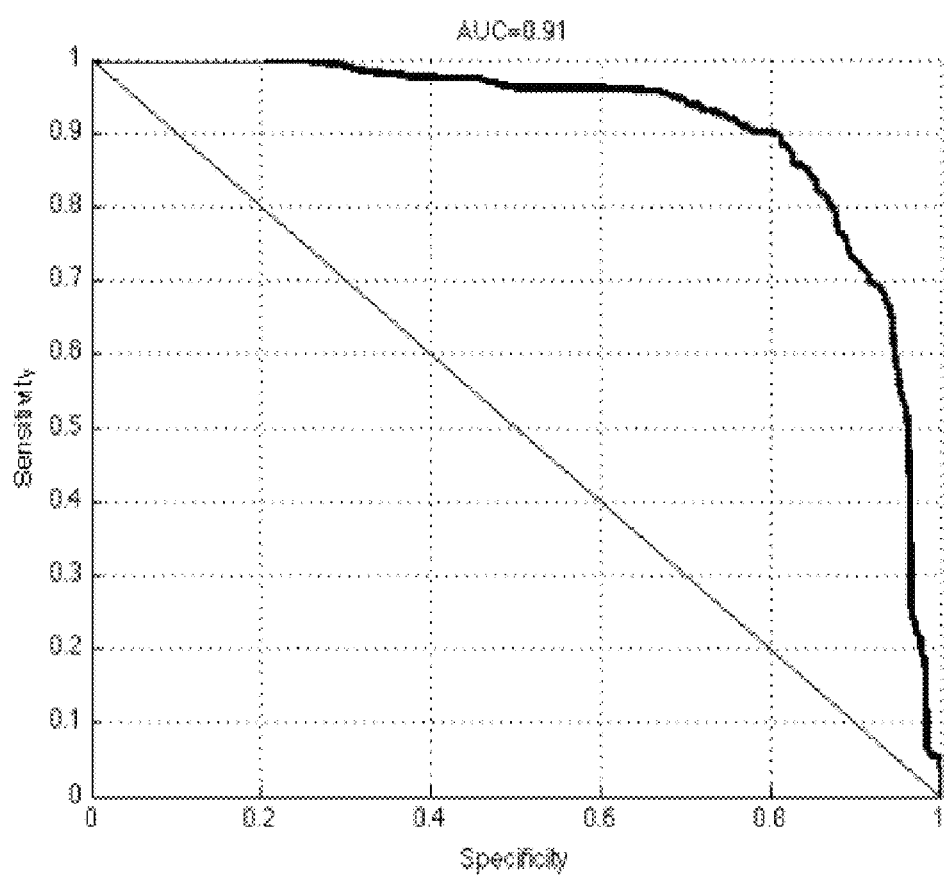
FIG. 11 is a receiver operating characteristic (ROC) curve for 10×10 cross-validation of the image classifier.

With 20×5-fold cross-validation, similar results were obtained:

AUC=0.913±0.007, BER=0.159±0.008. FIG. 11 shows the ROC curve for 10×10-fold cross-validation. It is noted that each of the individual classifiers A, B and C perform similarly with an AUC of 0.79.

Figure 12:
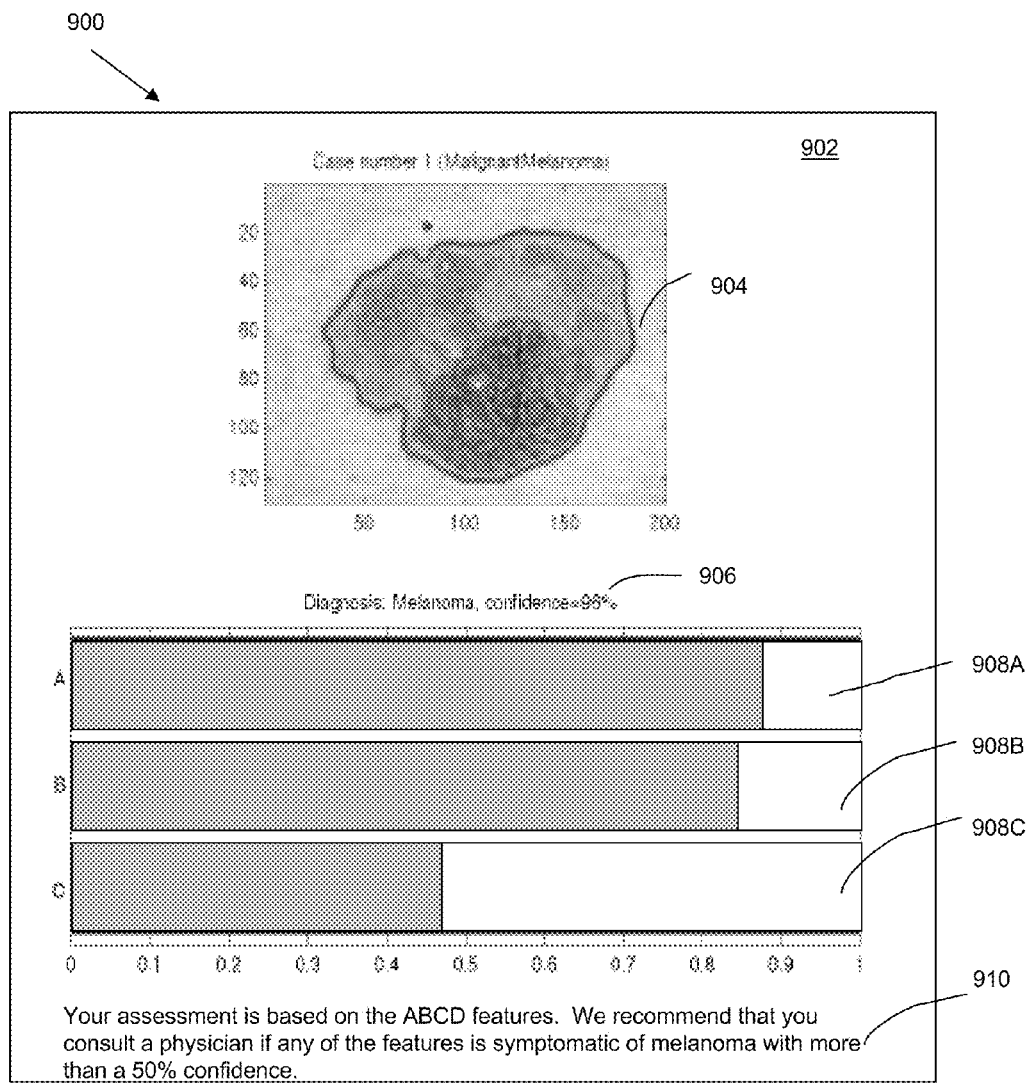
FIG. 12 is a sample report displayed to the user following classifier analysis of the image of FIG. 7.

The ensemble of classifiers that follow the ABCD diagnosis rules provides a good understanding of the decision made by each classifier. FIG. 12 illustrates an exemplary format for a sample report to the user showing the result of classification of the image that is shown in FIG. 7. At the upper portion 902 of the display window 900, the user name is provided along with a case number. The photograph that was submitted by the user is reproduced as image 904. The result of the ensemble classifier is displayed at 906 in the form of a confidence level that the suspected lesion is melanoma. In this example, the classification is Melanoma with 96% confidence. This number is the post-processed logistic regression probability value of the ensemble classifier. The lower portion of the figure shows the logistic regression probability values for the individual A, B and C classifiers as bar graphs 90A, 908B and 908C, respectively, showing the confidence level for the corresponding feature. (Note that a D classifier was not used in this example because dimensional data was not available from the test image dataset that was used.) From this particular example, it can be seen that asymmetry and border are more determinant factors than is color. The bottom of the exemplary display window includes a statement describing the basis for the assessment and provides a recommendation that the user consult a physician if any of the features is symptomatic of melanoma with more than 50% confidence. The message are the bottom of the display window may include a hyperlink to a different page that allows the user to enter their geographical location information to obtain a referral to one or more specialists who can further evaluate the suspected lesion. Alternatively, the geographical location information has already been provided to the central server, selecting the hyperlink with direct the user to a page that automatically displays the names and contact information for one or more specialists.

The ensemble classifier is a robust classifier in spite of the small dataset, and the data is not overfit. Additional classifiers were tried with similar results including kernel ridge regression (AUC=0.9178±0.0090, BER=0.1492±0.0109); naive Bayes classifier (AUC=0.9049±0.01, BER=0.1363±0.01); random forest classifier (AUC=0.9295±0.02, BER=0.10±0.03 (only 10 folds); logitboost AUC=0.9426±0.02, BER 0.1355±0.04 (only 10 folds); support vector classifier with recursive feature elimination (RFE) (AUC=0.08868, BER=0.1868).

The predictive power of the various features was evaluated using several feature selection algorithms that are available in the CLOP package: Pearson correlation coefficient (univariate, linear), Relief (univariate, non-linear), Gram-Schmidt (multivariate, linear, forward selection), RFE-SVM linear version (multivariate, linear, backward elimination) and RFFS Random Forests (multivariate, non-linear, bagging, forward selection).

Table 4 below lists the top ranking image features identified by the different feature selection methods with the top five of each method underlined:

TABLE 4

| Pearson | Relief | Gram-Schmidt | RFE-SVM | RFFS |
|---|---|---|---|---|
| radius_aspect | radius_aspect | radius_aspect | asymmetry | island1_clength |
| color_island_V | color_H | color_island_V | color_island_R | color_island_R |
| color_island_R | radius_cv | color_island_H | color_island_V | radius_aspect |
| island2_clength | color_island_H | color_island_R | color_island_H | asymmetry |
| radius_cv | asymmetry | island1_eccentricity | color_H | radius_cv |
| asymmetry | island1_clength | radius_cv | island1_clength | color_island_V |
| color_island_H | island2_clength | island1_clength | island1_eccentricity | island1_eccentricity |
| color_V | color_island_R | island2_clength | radius_aspect | color_H |
| color_R | color_island_V | asymmetry | radius_mean | island1_clength |
| color_island_G | color_R | color_R | color_G | color_island_H |

The following image features are selected by at least four out of five feature selection methods:

"A" Features
radius_aspect
asymmetry
"B" Features
radius_CV
island1_clength
island2_clength
"C" Features
color_island_V
color_island_R
color_island_H D features were not included in the above test because dimensional data was not available from the images in the initial test database. (Note that, as discussed below, the dimensional data may be obtained from the survey responses.) The three types of image features (A, B, C) are selected in the top ranking features. For the geometric features, the A (asymmetry) features appears to be more important than the B (border) features. For the color features, the color of the "island" appears to be a determining factor by way of its intensity relative to the surrounding area, its "redness", and its hue, which represents the color direction globally.

Figure 15:
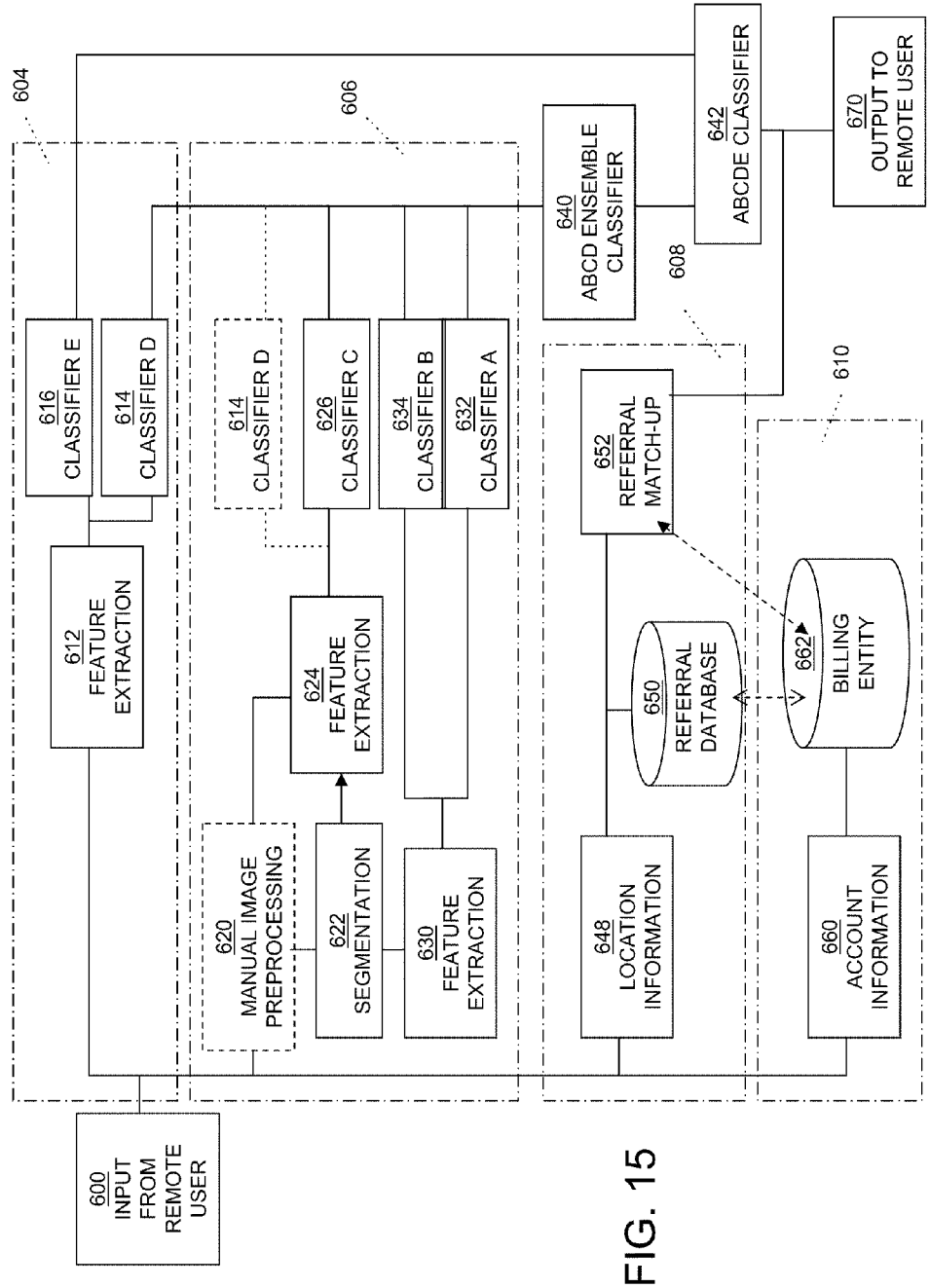
FIG. 15 is a block diagram of an exemplary multi-module construction for a remote melanoma screening system and method.

FIG. 15 provides a block diagram showing the modular and hierarchical arrangement of tasks for analyzing the combination of data obtained from the remote user of a smart phone or computer who wishes to obtain a preliminary screening for melanoma using the system and method of the present invention. The user input 600 includes the photograph(s) of the suspected melanoma sites, the survey data, the geographic location information and the (optional) account information for securing payment. The input 600 is downloaded to the image server for processing of the image and survey data in processing modules 606 and 604, respectively. The image analysis module 606 as illustrated includes manual image pre-processing 620, which is shown in dashed lines because it is actually performed by the user under instruction from the image server, and is not part of the image server process. The manually pre-processed image is segmented in step 622 after which the border and geometric parameters are extracted in step 630. These values are separated into A (asymmetry) and B (border) groups and input into their respective feature classifiers, Classifier A (632) and Classifier B (634). Using the borders detected in the segmentation step, the color features are extracted from the original (manually pre-processed) image in step 624 and input into Classifier C (626). If the dimensional information can be obtained from the image using the EXIF meta data, or if the user included in the photograph a dimensional reference such as a ruler, or a coin or other object of known dimension, the actual measurements can be extracted using the segmented image and input into Classifier D (614). Note that Classifier D is only indicated by dashed lines within image analysis module 606 because it may not be possible to obtain the dimensional data from the image. In this case, the dimensional data will be obtained through the survey data that is input into the survey processing module 604 of the image analysis server.

Survey processing module 604 receives the responses to the survey data. Table 5 provides one approach to obtaining relevant information from the user by way of a listing of possible survey features that have historically been recognized by practitioners as providing useful clues for diagnostic purposes and the questions that may be included in the survey.

TABLE 5

| Feature | Survey Question |
|---|---|
| Diameter D | What is the current diameter of the mole in millimeters? |
| | Answer "yes" or "no" to the following: |
| | This (existing or new) mole or freckle has been changing in: |
| S1: Size | size? |
| S2: Shape | shape? |
| S3: Color | color? |
| S4: Novelty | This mole or freckle appeared recently (less than a year) |
| S5: Ugly duckling | This mole or freckle looks different from those on the rest of my body. |
| S6: Sore | This mole or freckle has a sore that does not heal. |
| S7: Sensation | This mole or freckle feels different than it used to. |
| S8: Inflammation | This mole or freckle is inflamed. |
| | This mole or freckle is located on my _____. |
| S9: Body part - torso | torso? |
| S10: Body part - head | head? |
| S11: Body part - face | face? |
| S12: Body part - neck | neck? |
| S13: Body part - leg | leg? |
| S14: Body part - foot | foot? |
| S15: Body part - arm | arm? |
| S16: Body part - hand | hand? |
| | Fill in the blank of the following question: |
| S17: Geographic location | My residence city & state or mail (zip) code is _____. |

Figure 16:
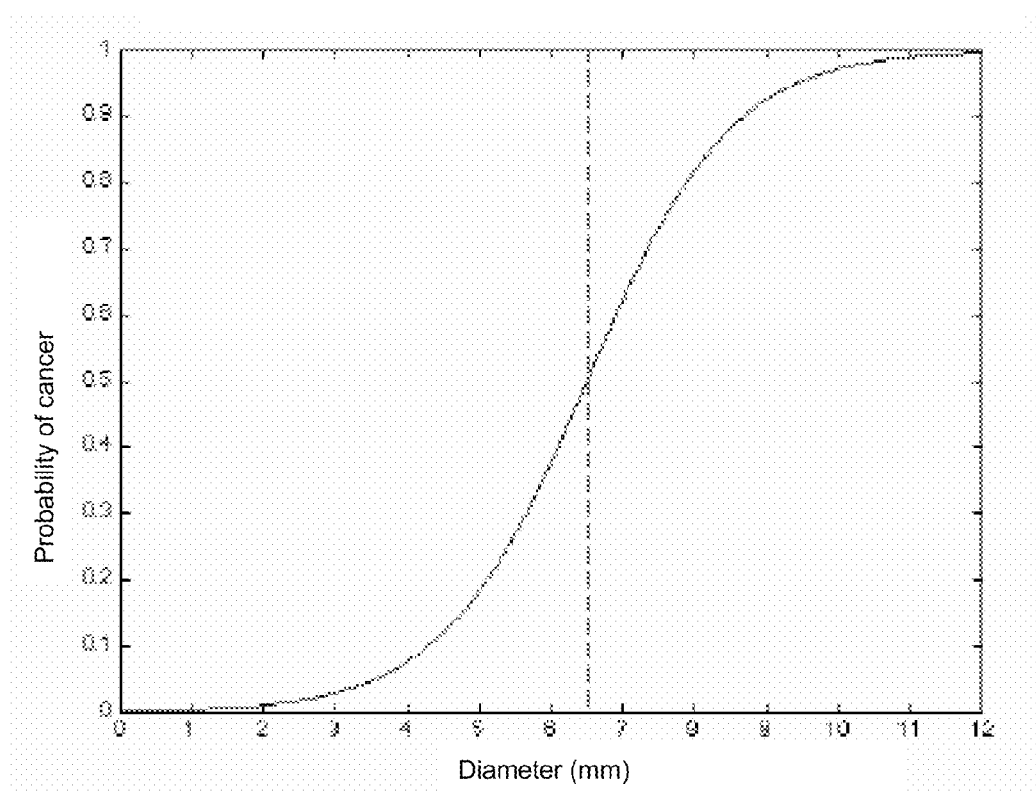
FIG. 16 is a plot of a sigmoid function for classification of mole or freckle diameter according to one embodiment of the invention.

The response to the question about diameter will be input into Classifier D (614). Based on a literature review, a threshold of 6 to 7 mm may be used to diagnose malignant melanoma based on size of the mole. Preferably, however, Classifier D would be a learning machine such as a support vector machine, random forest, linear logistic regression model (sigmoid) or other classifier that is trained with data having known outcomes. In an exemplary implementation, a sigmoid function is used for determining probability of cancer based on the relationship:

P(cancer)=$1/(1+\exp(-(ax+b)))$, where x is the diameter, a=1 and b=6.5, based on the literature findings. FIG. 16 illustrates the exemplary sigmoid function.

The results of each of Classifiers A, B, C and D will be input into ensemble classifier 640 to generate an overall result based on analysis of the image. This result will preferably be converted into a probability or percentage to provide the user with a risk score.

The survey answers will be extracted from the user survey response in the feature extraction process step 612 and input into a trained classifier (Classifier E (616)), which, as in the other classifiers, may be a support vector machine (SVM), random forest (RF), or other learning machine as is known in the art. The survey features S1 through S16 in the example shown in Table 5 are all binary. In an alternative embodiment, some or all of the survey questions can request an explanatory answer, with the survey providing a suggested format or multiple-choice options for the answer. For example, in lieu of binary questions S9 through S16, the survey could provide a list of options such as torso, head, neck, face, etc., possibly associated with a number, so that the user would enter either the word "neck" or the number, e.g., "3", corresponding to "neck." These responses can be combined with any binary values using a trained classifier such as SVM, RF or other learning machine.

Figure 18:
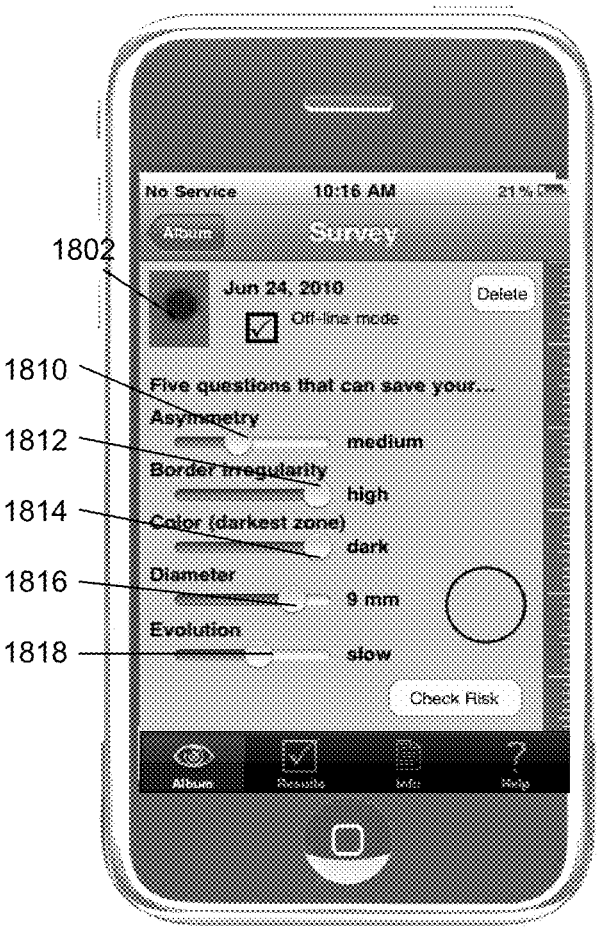
FIG. 18 is an image of a smart phone with an alternative survey display.

A possible drawback to a detailed survey with a series of questions such as those in Table 5 is that the user may lose interest if required to answer too many or too detailed questions. An alternative, simplified approach would be to use a survey that consists simply of the A, B, C, and D values, plus a possible fifth value "E" for evolution, which is a subjective description of how quickly the lesion has changed. FIG. 18 illustrates an example of such a survey. The display includes an image of the lesion 1802 so that the survey response can be matched up with the particular lesion of interest. When submitting the request in an on-line mode, elements A, B and C of the survey may be automatically entered by the system based on the values extracted during the pre-processing of the image that was downloaded prior to completion of the survey. The user then needs only to enter the information relating to diameter D and evolution E, which may be selected from within a range of no change to rapid change. This approach is ideal for use with a smart phone with a touch screen, where the user can select the value using a slider activated by dragging a finger across the screen. For diameter D, the user moves slider 1816 until the appropriate numerical value is displayed to the right of the slider. For evolution E, the user moves slider 1818 until the appropriate descriptive term appears next to the slider. When the survey is being completed in real time in an on-line mode, sliders 1810, 1812 and 1814 for A, B and C, respectively, may be disabled because the image analysis will fill in the values automatically. However, if the survey is being completed in an off-line mode, without the image having already been downloaded to the system for pre-processing, in addition to entry of the D and E values, the user may enter values for A, B and C manually using sliders 1810, 1812 and 1814. In an off-line mode, help screens may be provided to assist the user in selecting appropriate values for A, B and C. For example, a help screen for asymmetry can display: "A is for Asymmetry:

A mole is considered symmetric if it is roundly shaped. A mole may be oval, which is one kind of mild asymmetry. It can have no axis of symmetry at all." Sample images of asymmetric moles may be included. An example of a help screen for border is "B is for Border: An irregular border is an indication of malignancy, except for very small moles, which may have an irregular border due to the skin texture. Border distortions occur in pictures taken with insufficient light; take pictures outside with indirect light." A help screen for color may provide examples of different color ranges, while a diameter help screen may include labeled circles of different to allow the user to compare the mole to the circles to select the closest size circle.

In an alternative approach for combining binary survey results using expert knowledge of their relative importance, the methodology of the noisy-OR model (S. J. Russell and P. Norvig, *Artificial Intelligence: A Modern Approach*, Prentice Hall, 2003) may be used to map expert knowledge to parameters. This model makes simple independence assumptions between direct causes $X_i$, where i=1, . . . , n of a target Y. The influence of the $X_i$ on Y is parameterized by only n parameters $\pi$, which is intuitive to evaluate for experts. Using n intermediary influence variables $Y_i$ such that Y is the simple logical OR of the $Y_i$, the parameters $\pi$ represent the probabilities of successful influence: $P(Y_i=1|X_i=1)=\pi$ and $P(Y_i=1|X=0)=0$. Then, $$P(Y=1)=1-\pi_i(1-P(Y_i=1|X_i)). \quad (1)$$

The probability of cancer given the image evidence (or the survey for D) for the ABCD features can be obtained from a logistic regression model or can be combined similarly to the above equation.

Studies have shown that S1, S2 and S3 are major indicators of melanoma. In one study (McKie, 1990), the major indicators of changes in size, shape and color of a new or preexisting cutaneous lesion were seen in 94%, 95% and 89%, respectively, of the lesions evaluated. Using the values from this study, $P(X_i=1|Y=1)\sim 0.9$. This provides means for evaluating $\pi=P(Y_i=1|X=1)$. Based on U.S. government statistics from 2003 for melanoma (20 cases for every 100,000 people), $P(Y=1)$ can be approximated to be $2\times 10^{-4}$. In the illustrative example, a value of $\pi$ was selected somewhat arbitrarily as 0.45 for the major signs.

The following discussion and Table 6 below provide an example of a combination of results of the analysis of the individual features extracted from the image plus the survey questions by an ensemble classifier such as classifier 642.

Each column of Table 5, except for the last column, represents the probability of cancer given the single feature evidence for A, B and C obtained from FIG. 7 and the survey responses. For simplicity, survey responses are for S1-S8 only. These partial results are combined with the noisy-OR model of Equation 1 to produce the result provided in the last column. The rows represent three hypothetical mole diagnoses based on different possible survey responses in combination with the image of FIG. 7.

classifier 640 using the image data alone, which had diagnosed a 96% chance of malignancy. Thus, the model of Equation 1 appears to be overly sensitive, possibly due to an assumption of independence between variables. It is a known advantage of SVMs that they do not make independence assumptions. Thus, a better result can be obtained when ABCDE classifier 642 is SVM-based. In a preferred embodiment, both ensemble classifiers 640 and 642 will be SVMs.

The input from user 600 is also provided to the web server module 608, which extracts user information, including the geographical location in step 648. Alternatively, as described above, the geographical location can be automatically extracted from GPS information available from a smart phone with a GPS function enabled, or from EXIF data, if available. The geographical location is compared to a database containing physician or other healthcare provider information to identify practitioners within a certain distance of the user. The referral match-up operation 652 identifies providers who match the geographical location of the user and forwards the contact information and, preferably, distance information from the user's location to the provider's office, to be output to the remote user in block 670. For example, the information that is provided to the remote user is a list of physicians' names, their respective addresses, telephone numbers and distances, in miles or kilometers, from the user's geographical location.

Optional transactional module 610 receives information from the user 600 that allows a transaction to be conducted to secure payment for the analysis services. User information 600 will include a financial account number, which may be a credit card number, PayPal® account number, wireless service account number or other account to which a charge can be submitted and payment received. This account information will be communicated to a financial institution, e.g., bank, credit card company, PayPal®, wireless provider, etc., for entry into its database 622 to show a charge against the user's. Typically, the charge per transaction will be on the order of $2 to $20, however, provisions may be made to make a one-time payment to establish an account with the analysis service provider to allow the user to submit a fixed or unlimited number of inquiries. In this latter scenario, the account information that is transmitted will be the user's account with the analysis service provider. The web server will compare that account information with its own database to confirm that the user has an account that has been paid up or will be billed for the service. If the user's account has expired or is otherwise unavailable, the server will notify the user and no analysis will be performed until arrangements for payment have been made.

In an alternative approach, the user information provided to the transactional module 610 will be the user's geographical information which will be compared to information in the referral database 650. In this scenario, the provider(s) who would receive a referral based on a match-up of user's geographical location would have their own financial account

TABLE 6

| A | B | C | D | S1 | S2 | S3 | S4 | S5 | S6 | S7 | S8 | P |
|---|---|---|---|---|---|---|---|---|---|---|---|---|
| 0.87 | 0.85 | 0.46 | 0 | 0 | 0 | 0 | 0 | 0 | 0 | 0 | 0 | 0.9895 |
| 0.87 | 0.85 | 0.46 | 0.3 | 0 | 0 | 0 | 0 | 0.15 | 0 | 0 | 0.15 | 0.9947 |
| 0.87 | 0.85 | 0.46 | 0.8 | 0.45 | 0 | 0 | 0 | 0.15 | 0 | 0 | 0.15 | 0.9992 |

Using Equation 1, even with no survey results, the probability (risk score) is higher than that determined by ABCD charged for the analysis service. Thus, the analysis service would be an advertising or marketing expense for the provider. In this case, the provider could be the physician who would treat the user, or it could be a diagnostic laboratory that has contracted with one or more physicians to whom the user would be referred under the assumption that the physician would send pathology samples to the laboratory for analysis, for which the laboratory would be compensated by the patient or the patient's insurance.

Once the payment has been secured, if any, the results of the analysis plus other useful information for interpretation of the result will be transmitted to the user in block 670 along with the referral information for healthcare providers that are identified in the referral match-up 652.

FIGS. 17a-17d illustrate exemplary content that can be displayed on a smart phone such as an iPhone® or similar touch screen Internet-capable phone. The smart phone implementation may have several main functionalities. A welcome page will be displayed when the smart phone user initially accesses the application. The welcome page will include basic information about the service and will have icons for selecting different pages. In one embodiment, if no icon is "clicked", after 3 seconds, the application will switch automatically to the camera page.

Figure 17A:
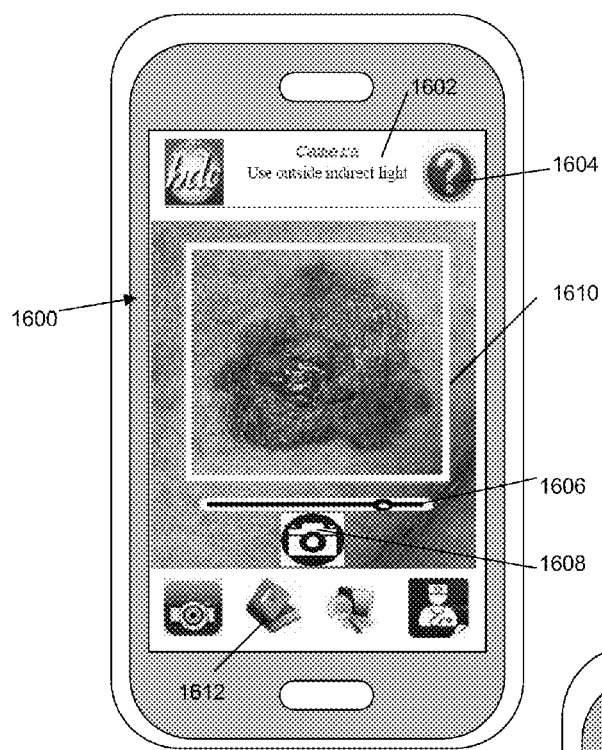
FIGS. 17a-17d are images of a smart phone with sample displays produced according to one embodiment of the invention.
Figure 17B:
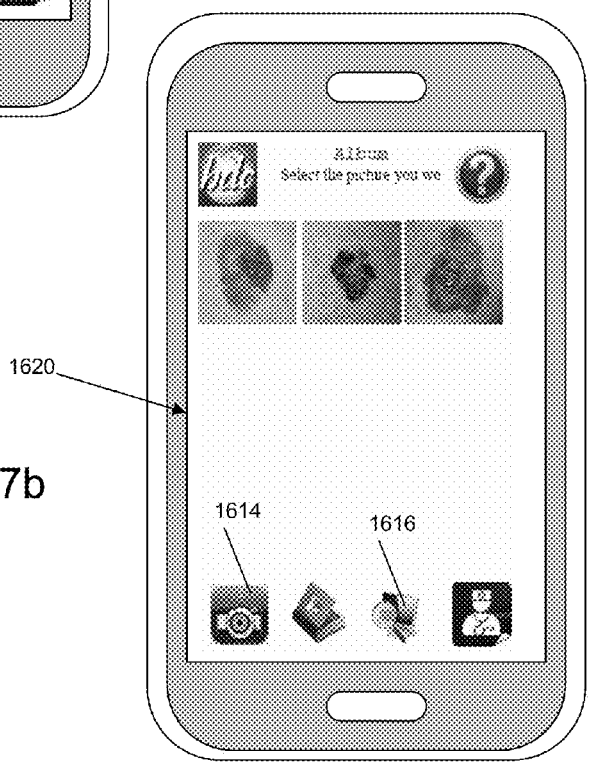

The "camera" page 1600, illustrated in FIG. 17a, allows the user to take photographs. The functionality of the camera software of the application will include allowing the user to zoom and take pictures using auto focus. The goal is to obtain an image as close as possible to raw data, preferably in a non-compressed format. The auto focus information will be records to allow the image processor to determine the distance of the camera from the lesion. The zooming factor should also be recorded. In addition, feedback may be given to the user to allow him or her to take better pictures. The feedback may include illumination ("is there sufficient light?"), jitter and blur ("is the camera or the body part moving?"), focus ("is the camera far enough from the lesion to allow the auto-focus to work properly?"), and framing ("is the mole well-framed in the square?", referring to a square displayed at the center of the screen to assist in centering and zooming the image).

Brief instructions will be displayed in a box or ticker 1602 at the top of the page to assist the user in setting up the photograph for optimal clarity. Sample instructions may include "Use outside indirect light. Rest camera on support 3 inches (8 cm) away from mole. Zoom to fit framing rectangle (or center mole and zoom to max)" A "help" button 1604 can be pressed to obtain more detailed instructions. A slider 1606 allows the user to zoom the camera to fit the frame 1610, which is displayed on the screen. When the user is ready, he or she clicks on the camera button 1608 to take the photograph. Once the picture has been taken, the user is automatically sent to the "album" page 1620, shown in FIG. 17b. Alternatively, the user can click on the album icon 1612 at the bottom of the page.

Album page 1620 displays images 1622, 1624 and 1626 that have already been take by the user. A ticker or banner at the top of the page instructs the user to "Select the picture you would like to send for diagnosis, or go back to the camera to take another picture." If the user wishes to take another photograph, he or she will click on the camera icon 1614. If the user is satisfied with the photographs and has taken photographs of all of the suspicious moles, the user clicks on one of the images to be automatically directed to the "send" page.

The send page (not shown) allows the user to zoom the image, delete the image, go back to the album page 1620, or send the image to the image analysis server for analysis after responding to the survey questions that are displayed on the send page. After completion of the survey and selection of one or more image, the user can click on the send icon 1616 to transmit the photograph and survey data to the image analysis server.

Figure 17C:
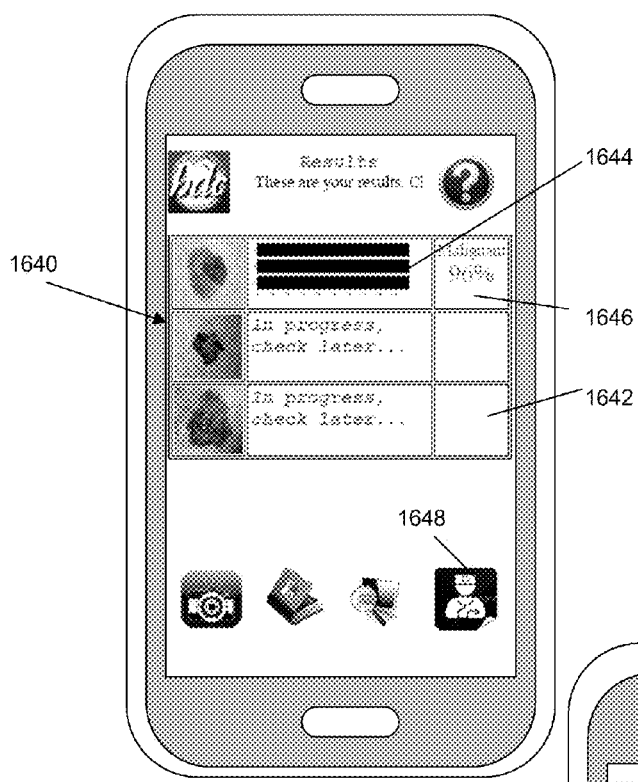
Figure 17D:
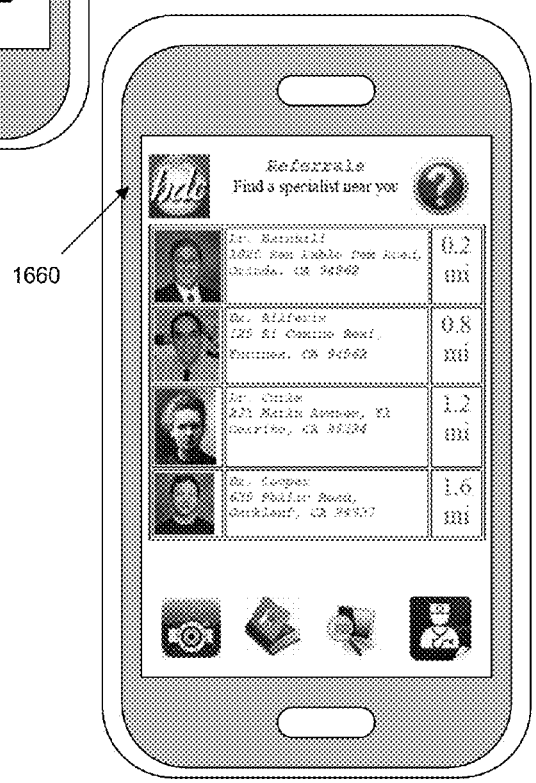

As soon as the image and survey data have been received, the display will automatically change to the results page 1640, shown in FIG. 17c. The ticker or box at the top may display a message, "These are your results. Check periodically for updates". In the sample display, a table 1642 is shown with rows corresponding to three different images. The second column 1644, first row displays a set of bar graphs corresponding to the classification results of the individual ABC feature classifiers, such as the example shown in FIG. 12. The third column 1646 provides the risk score which, for the first image, is a 96% probability of melanoma. The second and third rows are shown as being "In progress" because the image analysis server is still analyzing the images. Once the analysis if completed, the table will be updated and the results will be displayed in the same format as shown in the first row of the table.

The user can obtain referrals to physicians by pressing the physician icon 1648 from any of the other pages. The referral page 1660, shown in FIG. 17d, may display one or more (if available) physicians in the area, providing a table with the name, address and telephone number of the physician, an optional photograph, if available, and the approximate distance from the user's location to the physician's office. Optionally, the physician information may include a live link that will automatically dial the physician's office telephone number when the user clicks on the contact information in the second column or on a separate "call" button that may be displayed as a fourth column (not shown) in the table.

The following examples describe alternative procedures that may be used in conjunction with the inventive system.

Example 1

Classifier Variation

Using a set of cropped images obtained from the DERM-NET™ skin disease image atlas (available on the World Wide Web at dermnet.com), the recognizer that was used in the ABCD analysis described above with reference to FIG. 14, was re-trained and tested. Malignant samples (Malignant Melanoma and Lentigo Maligna) were separated from all other samples, including some very ambiguous ones that mimic melanoma.

Five-fold cross-validation experiments were performed using the same four classifiers that were used in the garbage image classification processing described above. The four classifiers were Naïve Bayes, Linear kernel, Polynomial—$2^{nd}$ degree (Poly 2) kernel, and RBF kernel, were used to process the previously-described data representation of ABC features. The best result was obtained using a linear kernel, with AUC=0.78. An ensemble classifier voting was tested on classifiers trained independently on A, B, and C features yielding AUC=0.75. An AUC of 0.80 was obtained using a linear kernel with the new data representation described with regard to the garbage image classification (note that this representation was not designed for separating skin disease samples and involves no segmentation.) A combination of both representations yielded AUC=0.82.

These results and, and errors made in test runs, lead to the conclusion that:

The ABC features often fail because of poor segmentation because the mole outline cannot be found. Consequently, the features designed for separating garbage from skin disease, which involve no detection of mole outline, work as well or better.

Adding yet more features may help. For example, a number of mistakes are due to the presence of hairs. Thus, hairs may need to be removed, or a texture analysis may be appropriate.

The linear kernel recognizer does not overfit data. When trained on all the data on the ABC features, the AUC obtained on training data is 0.8.

An approach was developed to build two risk assessment systems: one for the risk associated with the personal profile (e.g., age, skin color, family history, eye color, use of sunscreen, etc.) and one for the risk associated with the particular mole. To validate the system, data was collected by taking pictures of moles available on the Internet using a smart phone camera, in this case, an iPhone®. The photographs were taken directly from the computer screen display at a distance of about 40 cm from the screen to avoid aliasing. The image on the screen was displayed in a larger size than 1 to obtain a better resolution. The collected image set consisted of 185 images including 25 "garbage" images, 50 melanoma images, 42 non-melanoma moles, and 68 images of other skin diseases, including squamous cell carcinoma and basal cell carcinoma).

The ABC and garbage image recognizers were integrated into a single system and combined with the D and E features. The user is provided ABCDE scores and an overall risk assessment: Low, Medium, or High.

The quality of the smart phone images was such that a few rejection criteria were added to eliminate bad images. An image would be rejected if any of the following criteria were met:

a) The "garbage" classifier identifies a "garbage" image.
b) The color feature C is lower than 0.2.
c) The area of the mole relatively to the area of a round mole of the same diameter is lower than 0.5 or larger than 1.2.
d) The fraction of the mole falling inside the framing square is lower than 0.3.
e) There is a larger fraction of the mole outside than inside the framing square.

The A, B, and C recognizers trained with the CLOP models from subsets of lower level features produce the A, B, and C feature scores:

model_A=chain({standardize, fixed_fs(A), naive, klogistic});
model_B=chain({standardize, fixed_fs(B), naive, klogistic});
model_C=chain({standardize, fixed_fs(C), naive, klogistic});

The D feature is obtained from the diameter d using a squashing function:

$$D=1/(1+\exp(-(a \cdot d+b)));$$

with a=1 and b=−6.5.

In the present test, the E feature was the average of survey.recent, survey.size_change, survey.shape_change, and survey.color_change. Alternatively, the survey may ask for speed of evolution, which is a metric frequently used by dermatologists to determine the aggressiveness of the tumor.

The following risk values were assigned: Low=0, Medium=1, High=2. Three risks were produced for the ABC features, the D feature, and the E feature, then all features were combined into an overall risk.

To obtain the ABC risk, a recognizer trained globally on the ABC features was used following the CLOP model (model=chain({standardize, kridge, bias})

| | | |
|---|---|---|
| ABC_output > $\theta_2$ | → | ABC_risk = High (2) |
| $\theta_1$ <= ABC_output <= $\theta_2$ | → | ABC_risk = Medium (1) |
| ABC_output < $\theta_1$ | → | ABC_risk = Low (0) |

To obtain a D risk, the diameter d was thresholded:

| | | |
|---|---|---|
| d ≥ $\theta_4$ | → | D_risk = High (2) |
| $\theta_3$ ≤ d ≤ $\theta_4$ | → | D_risk = Medium (1) |
| D < $\theta_3$ | → | D_risk = Low (0) |

To obtain the E risk, the E value was thresholded:

| | | |
|---|---|---|
| E > 0 | → | E_risk = High (2) |
| E = 0 | → | E_risk = Low (0) |

(Note: no answer is the same as E = 0.)

The thresholds $\theta_1$ and $\theta_2$ were set using the validation data to obtain a reasonable compromise between false positive and false negative: $\theta_1$=−0.1 and $\theta_1$=0.5.

For the mole size, data from the literature indicate that moles under $\theta_3$=2 mm are usually considered very low risk. Moles of size over 5 to 8 mm are usually considered high risk. The size threshold varies according to the references. For purpose of this test, a threshold of $\theta_4$=6.5 was chosen. The threshold of 6.5 corresponds roughly to the optimum balanced error rate. Under that threshold, the risks were combined as follows to obtain the overall ABCDE risk:

| | |
|---|---|
| ABCD_risk = 0 | if D_risk = 0 |
| ABCD_risk = max(0, ABC_risk − 1) | if D_risk = 1 |
| ABCD_risk = ABC_risk | if D_risk = 2 |
| ABCDE_risk = ABCD_risk | if E_risk = 0 |
| ABCDE_risk = min(ABCD_risk + 1, 2) | if E_risk > 0 |

The results in Tables 7 and 8 show ABC features only and ABCDE features, respectively. There were no false negatives (melanoma cases found low risk) and a few false positives. Adding the D and E features improves the results, but not significantly. The fraction of rejected pictures is rather high due to partly to the low quality of the images and the large number of non-mole images (that are correctly rejected since the classifier focuses on evaluating the risk of melanoma for moles.

TABLE 7

| Category | Rejected | Low | Medium | High | Total |
|---|---|---|---|---|---|
| Garbage | 15 | 1 | 5 | 4 | 25 |
| Melanoma | 19 | 0 | 9 | 22 | 50 |
| Moles | 16 | 8 | 14 | 4 | 42 |
| Other | 59 | 0 | 2 | 7 | 68 |

TABLE 8

| Category | Rejected | Low | Medium | High | Total |
|---|---|---|---|---|---|
| Garbage | 15 | 1 | 5 | 4 | 25 |
| Melanoma | 19 | 0 | 7 | 24 | 50 |
| Moles | 16 | 11 | 10 | 5 | 42 |
| Other | 59 | 0 | 7 | 2 | 68 |

Example 2

Modified Pre-Processing

The DERMATLAS image dataset from Johns Hopkins University (available on the World Wide Web at dermatlas.org) was used to extract 1000 images of skin diseases with various diagnoses, including herpes, acnea, drug reactions, insect bites, squamous cell carcinoma, basal cell carcinoma, congenital nevi, other benign moles, and melanoma. Associate with the images are annotations both in the form of MS access database and MS Excel spreadsheets. The annotations include age and gender of the patient, data source information, and diagnosis.

Software was written to crop the images into 1717 cropped pictures (some coming from the same image). The software also allows a framing box to be drawn around the lesion, such as described above with reference to FIG. 17a. The framing box facilitates segmentation of the mole from the background and is in a similar form to the data that would be collected using the smart phone application.

The original annotations do not include a database entry for lesion size or diameter and for lesion evolution, which are needed for accurate classification. However, the database includes comments that often have an indication of size and/or evolution. Furthermore, the non-cropped image permits determination of the context and evaluation of the scale. A data browser was written to visualize the data and the annotations, and to allow editing of the annotations, thus permitting the extraction of approximate values of size and evolution for every cropped image. Such values are not very accurate, but, they provided a significant improvement in classification performance.

The following methods were employed for determining the mole size:

a) If there was a scale on the image itself, it was used.
b) If there is no scale on the image but there is a size value in the comments, that value was used after making sure that the size corresponds to the size of what was identified as a lesion.
c) If there is no scale and no indication in the comments, but whole body parts can be seen, the size was estimated relative to the body parts.
d) If none of the above were available, clues such as the skin texture or hairs were used to estimate the size.

If several indications were given, they were cross-verified consistency and to calibrate the heuristic method.

The following method was used to extract the evolution information from clues in the comments. There are three evolution categories:

1. None: This is a congenital nevus or birth mark reported to have changed "little" or not at all since birth or has grown proportionally with the patient.
2. Slow: This is a nevus (mole) that appeared since birth (usually due to sun exposure) or this is a non-melanoma cancer. There is either no mention of how fast the lesion grew or the word "slow" appears in relation to growth description, or it appears from the description that the evolution has taken years (not months).
3. Fast: The word "fast" appears in relation to growth description, or it appears from the description that there has been a fast evolution in the last few months. If the diagnosis is that of an infectious disease or drug eruption or insect bite, but there is no mention of evolution, it is also categorized as fast.

Image segmentation is used to isolate the mole from its background. This tends to be a difficult step because of the high variability of the images. The sequence below was used to find a mask outlining the mole.

Input the image im
Create gsim a gray level image (we substituted our code here)
Create a multicolor gradient of im called grad
Compute the histogram of gsim and the distribution of the histogram
Compute the co-occurrence matrix in gsim
Threshold the co-occurrence matrix based on maximal entropy
Take a higher threshold for marking objects
Classify pixels of gsim using the threshold
Use the classification obtained and grad to mark the image
Watershed segmentation on the marked image
Classify regions To further simplify segmentation, the search for a lesion contour was limited to an area slightly larger than the framing box (a border of ⅕ of the width or height is added around the framing box). If several lesions were present in the area of interest, only the largest lesion was retained.

In order to avoid making incorrect decisions about the risk of melanoma because of image segmentation, a number of rules were introduced to declare a "No call" for images, which are either ambiguous or have a lesion outline such that segmentation is suspect:

Not a mole: Before segmenting the image, a classifier trained to separate images of moles from mixed types of photographs (garbage images, unrelated to skin disease) was run. The features used to perform such classification do not require segmenting the image (presence of a blob in the center, image symmetry, color histogram).

Suspicious contour: the lesion contour is not well centered in the framing square, too small or too large compared to the green square, or partly outside the framing square.

Low contrast: images which have a small contrast between lesion and surrounding background.

The above segmentation algorithm provided improved performance by reducing the "No call" by 10% among all the images and by 25% among the melanoma images (Tables 9 and 10). However, a few errors still occurred. Mistakes included: a) part of the mole was not included in the contour; b) surrounding objects, clothes or background were taken either as reference skin color or as mole instead of the real skin or mole causing the contour to be incorrect; c) the lesion was not a single mole but a group of moles, a cluster or a plaque; d) hairy nevi caused the software to confuse background and mole; and e) shading or glare.

Note that even when there was a segmentation error, the resulting decision of the classifier is not erroneous because it returns a "No call" or "Low contrast" (a special kind of No call).

Figure 20:
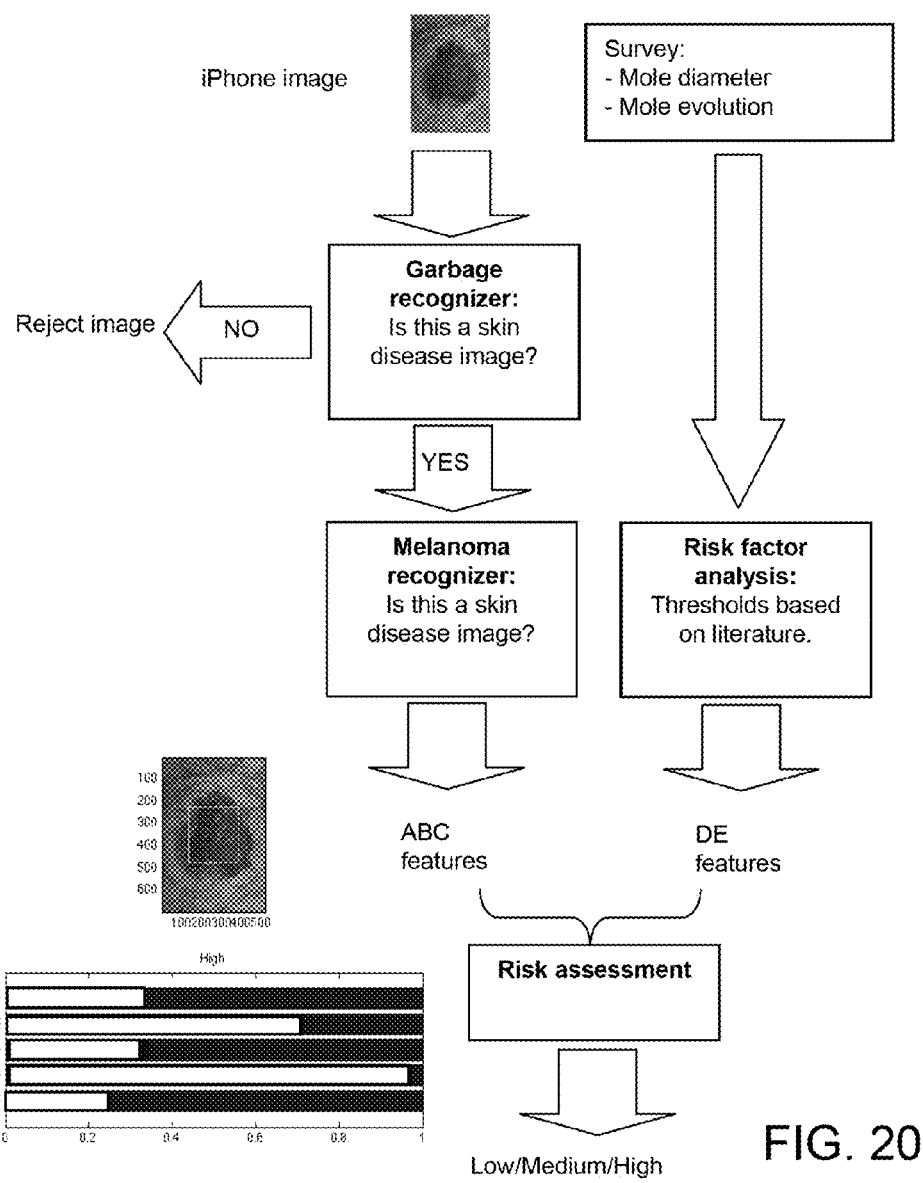
FIG. 20 is a flow diagram of an embodiment of the risk analysis system of the present invention.

A global index of risk of melanoma was built from the ABCDE features. (FIG. 20 is a flow diagram of the ABCDE risk analysis system in which the image is provided by a user with an iPhone®.) A classifier was not trained in all features because there were few cases of melanoma in the database—only about 30 of which are "typical" cases that can be classified with this method (the other melanoma cases include ulcers, metastases and nails). Instead, the data was used for testing only, and a heuristic formula was used to build an ABCDE classifier from the ABC classifier and the D and E features:

$$ABCDE = ABC + D + 2E$$

In this formula, ABC is the output of the ABC classifier, D is obtained from the diameter (after passing it through a squashing function to normalize it between 0 and 1) and E is 0.1 for non-evolving moles, 0.5 for slow evolution, and 0.9 for fast evolution. A larger weight was assigned to the E feature to give a similar importance to the geometrical features ABCD and the evolution E.

The predictive power of the various features in the separation "melanoma" vs. "benign moles" was evaluated. In this experiment, the ABCDE index was used to calculate the ROC curves and the AUC, without any rejection ("No call"). The melanoma cases and the benign mole include many types images that the classifier ABC was not trained on (images of large congenital nevi, halo nevi, ulcerated lesions, nodules, nails). Nonetheless, the classifier ABCDE does very well (AUC=0.94) and significantly better than classification using only ABC or any of the features taken individually.

The index ABCDE was normalized between 0 and 1 and two thresholds were set:
Index<0.4→Low risk
0.4≦Index≦0.6→Medium risk
Index>0.6→High risk There were 3 subgroups of "No call":
Low contrast: not a lot of difference between background and lesion so the contour is imprecise.
Borderline: Color not suspicious, but ABCDE index indicates medium of high risk.
No call: all the other cases of no call due to segmentation errors.

It should be noted that the "Borderline" category was introduced in an effort to reduce the number of false positives and false negatives. It plays the role of a buffer like the "medium" risk category, but is based on a different criterion. While this may be a useful distinction, it can be lumped with the "medium" category. Similarly, "Low contrast" could be lumped with "No call", but it falls in between "Low risk" and "No call".

The results are shown in Tables 9 and 10, which show the number of examples in a confusion matrix. Truth values are shown horizontally and risk assessment vertically. Comparing the old (Table 9) and the new preprocessing (Table 10), the new preprocessing decreases the number of "No call" classifications without increasing significantly the number of errors, and false negative are reduced. The answers were rated as very good, acceptable and bad, which are indicated in the tables as "A+", "A" and "B", respectively.

For lesions that are not moles (on which the classifiers were not trained, one would expect either one of the 3 types of "No call" or a "Low risk". Medium or high risk would be errors.

For benign moles, either "Low contrast" or "Low risk" would be expected. Because there are many types of nevi that were put into the mole category but were not really moles (not dark color, large plaques, halo nevi, hairy nevi, etc.) a "No call" or Borderline" assessment is acceptable. Since some nevi are actually worrisome, a "Medium" risk assessment is also acceptable. Thus, only "High" risk was considered to be an error, even though some of the moles in this category were sufficiently worrisome that the doctors requested a biopsy.

For "Other cancer" there is no real wrong answer. Any of the "No call" or "Low risk" categories should be expected, but "Medium" risk or "High" risk is an acceptable assessment because skin cancers should still be evaluated by a dermatologist, even if the referral was made for the wrong reason.

For "Melanoma", the cases would preferably be rated as "High risk". However, "Medium risk" is acceptable and any of the "No call" categories are acceptable as well, particularly because there are many melanoma images of cases that are not moles. The unacceptable bad error in this category would be a "Low risk" assessment.

TABLE 9

|  | Not a mole | Benign mole | Other cancer | Melanoma | Total |
|---|---|---|---|---|---|
| No call | 305 (A+) | 205 (A) | 102 (A+) | 40 (A) | 652 |
| Low contrast | 420 (A+) | 191 (A+) | 27 (A+) | 6 (A) | 644 |
| Borderline | 53 (A+) | 41 (A) | 12 (A+) | 2 (A) | 108 |
| Low | 21 (A+) | 173 (A+) | 2 (A+) | 3 (—) | 199 |
| Medium | 8 (—) | 23 (A) | 1 (A) | 1 (A) | 33 |
| High | 27 (—) | 20 (—) | 11 (A) | 23 (A+) | 81 |
| Total | 834 | 653 | 155 | 75 | 1717 |

TABLE 10

|  | Not a mole | Benign mole | Other cancer | Melanoma | Total |
|---|---|---|---|---|---|
| No call | 261 (A+) | 193 (A) | 100 (A+) | 30 (A) | 584 |
| Low contrast | 444 (A+) | 178 (A+) | 33 (A+) | 8 (A) | 663 |
| Borderline | 64 (A+) | 55 (A) | 8 (A+) | 9 (A) | 136 |
| Low | 23 (A+) | 178 (A+) | 1 (A+) | 0 (—) | 202 |
| Medium | 10 (—) | 30 (A) | 1 (A) | 1 (A) | 42 |
| High | 32 (—) | 19 (—) | 12 (A) | 27 (A+) | 90 |
| Total | 834 | 653 | 155 | 75 | 1717 |

Looking at the results in Table 10 (the best results), it can be seen that: out of 834 examples of lesions that are not moles, only 10 are wrongly classified as "Medium risk" and only 32 as "High risk"; out of 653 examples of benign moles (those include large nevi not trained on), only 19 examples are wrongly classified as "High risk"; and out of 75 examples of melanoma, only one is classified as "Medium risk" and none as "Low risk".

The errors were examined in an effort to identify the causes. For false positive examples, i.e., non moles or benign moles identified as melanoma medium or high risk:
Problem with glare and/or shade: 1%
Genuinely worrisome lesion (because of shape, color, dimensions or evolution): 36%
Lesion with relief (giving the illusion of an irregular contour or different color shades): 11%
Crusted blood: 17%
Cluster or grouped moles (creating an irregular contour): 35%

Among the false negative examples, which were no calls that should have been classified as melanoma:
No clear outline or light color (lentigo or SSM): 15%— (Note: these pose great diagnosis difficulty to doctors.)
Ulcerated skin: 13%
Segmentation error: part of the mole is not detected because there are either several clusters or large differences in color between regions: 14%
Nail: 11%
Hair: 7%
Glare/shades/poor light: 9%
Foreign object (clothing) present in the image: 5%
Large surface uniformly black or not enough border: 12%
Nodule: 14%

For the no calls (nevi/moles):
Large congenital nevi: 81%
Too small in framing square, e.g. halo nevi: 5%
Hairy nevi: 4%
Foreign objects: 2%
Shades and glare: 1%
Cluster or plaque: 3%
Other: 4%

With each risk assessment, the inventive system gives a recommendation or comment, which provides more details about how the decision was made and whether to consult a doctor. With this comment, a meaningful assessment can be provided, even in the case of the three "no call" cases (Borderline, Low contrast, and No call).

The Table 11 provides a few examples of comments that might be provided:

TABLE 11

| RISK | COMMENT |
| --- | --- |
| ** HIGH ** | Rapidly evolving skin lesions are always worrisome whether they are cancer or not. Based on the ABCDE features, your lesion presents a high risk of malignancy. We recommend that you consult a dermatologist. *IMPORTANT: If you are in a high risk category including if Melanoma runs in your family or you have a history of Melanoma, you should be regularly followed by a dermatologist. Most cases caught early can be cured, but Melanoma is a deadly disease. Do not neglect to take care of yourself. Keep watching for moles that increase in diameter and/or change in shape or color. |
| ** MEDIUM ** | Based on the ABCDE features, your lesion presents a non negligible risk of malignancy. We recommend that you consult a dermatologist. |
| ** LOW ** | Based on the ABCDE features, your lesion still presents a low risk of malignancy, but keep watching for increases in diameter and changes in shape or color. |
| ** BORDERLINE ** | Based on color alone, this lesion should be either a benign mole or not a mole. Based on the ABCDE features, your lesion presents a [xxx] risk of malignancy. We recommend that you consult a dermatologist. |
| ** LOW CONTRAST ** | The area of interest has a low intensity or low contrast. Your skin lesion may not be a mole (a dark spot on the skin) or your picture was not taken with enough light. Get good lighting: outside natural indirect light is best. Based on the ABCDE features, your lesion presents a [xxx] risk of malignancy. We recommend that you consult a dermatologist [except if xxx is not low]. |
| ** NO CALL ** | This image does not appear to resemble the picture of a mole. Moles are isolated dark spots on the skin which vary in size, but do not cover extensive areas. Several reasons may cause our software not to recognize your lesion as a mole. Try to isolate it from other neighboring moles and avoid including elements in the pictures that are not a mole or immediate surrounding skin. Isolate a single mole. Get good lighting (outside natural indirect light is best) and avoid shade and glare. Get good support (avoid jitter). Place the camera at a distance of the mole of about the iPhone length and zoom to fit the mole tightly into the green square. If you have a lot of hair, shave them around the region of interest. Based on the ABCDE features, your lesion still presents a [xxx] risk of Melanoma . . . |
| ** NO CALL ** | This image does not appear to resemble the picture of a mole. Moles are isolated dark spots on the skin which vary in size, but do not cover extensive areas. Several reasons may cause our software not to recognize your lesion as a mole. Try to isolate it from other neighboring moles and avoid including elements in the pictures that are not a mole or immediate surrounding skin. Isolate a single mole. Get good lighting (outside natural indirect light is best) and avoid shades and glare. Get good support (avoid jitter). Place the camera at a distance of the mole of about the iPhone length and zoom to fit the mole tightly into the green square. If you have a lot of hair, shave them around the region of interest. Based on the ABCDE features, your lesion still presents a [xxx] risk of Melanoma . . . |
| ** NO CALL ** | The part of the picture identified as a candidate mole has a very small surface compared to a circle with the same diameter. This may be due to a segmentation error of our program. We recommend that you take another picture with a good light and make sure to fit the mole tightly into the green square. Avoid including in the picture elements that are not a mole or surrounding skin. Avoid shades and glare. Isolate a single mole. Based on the ABCDE features, your lesion presents a [xxx] risk of Melanoma . . . We recommend that you consult a dermatologist. |

*The language following "IMPORTANT" may be added to each comment category.

The system and method of the present invention provide a free or low cost preliminary skin cancer screening capability that is accessible to the average person with a smart phone or a digital camera and Internet access. The analytical services provided according to the invention are not intended to replace evaluation and diagnosis by a physician specializing in skin cancer, but are merely intended to assist an individual to determine whether they should see a physician for evaluation of an area of the skin that is of concern.

REFERENCES

Incorporated Herein by Reference

Michal Antkowiak, Artificial Neural Networks vs. Support Vector Machines for Skin Diseases Recognition, Master's Thesis in Computing Science, Umea University Department of Computing Science, Sweden, May 2006.

Marco Burroni, et al. Melanoma Computer-Aided Diagnosis: Reliability and Feasibility Study, *Clinical Cancer Research*, Vol. 10, 1881-1886, Mar. 15, 2004.

Cynthia Cohen, et al. Mitogen-actived Protein Kinase Activation Is an Early Event in Melanoma Progression, *Clinical Cancer Research. Vol.* 8, 3728-3733, December 2002.

Stephan Dreiseitl, et al A Comparison of Machine Learning Methods for the Diagnosis of Pigmented Skin Lesions. *Journal of Biomedical Informatics*, Volume 34, Issue 1, February 2001, Pages 28-36.

Fikret Ercal, et al., "Neural Network Diagnosis of Malignant Melanoma From Color Images", *IEEE Transactions On Biomedical Engineering*. Vol. 41, No. 9, September 1994.

Rona M Mackie, "Clinical recognition of early invasive malignant melanoma. Looking for changes in size, shape, and color is successful", *BMJ*, Vol. 301 3, pp 1005-1006, November 1990.

Matthew M. Fleming, et al., "Image Analysis Cytometry of Dysplastic Nevi", *Journal of Investigative Dermatology*, Vol. 95:3, pp 285-291, September 1990.

Julie Gachon et al., "First Prospective Study of the Recognition Process of Melanoma in Dermatological Practice", *Arch Dermatol.* 2005; 141:434-438.

Haraled Ganster. "Automated Melanoma Recognition", *IEEE Transactions On Medical Imaging*, Vol. 20, No. 3, pp. 233-239, March 2001.

Ilias Maglogiannis and Elias Zafiropoulos, "Characterization of digital medical images utilizing support vector machines", *BMC Medical Informatics and Decision Making* 2004, 4:4.

Ilias Maglogiannis, Elias Zafiropoulos, and Christos Kyranoudis, "Intelligent Segmentation and Classification of Pigmented Skin Lesions in Dermatological Images", in G. Antoniou et al. (Eds.): SETN 2006, LNAI 3955, pp. 214-223, 2006. Springer-Verlag.

Serruys, et al, "Classification of skin tumors by an adaptive approach grounded on a learning-by-sample process. Application to the detection of melanomas", SPIE's Int. Tech. Gr. Newsletter 10, 1-3. 1999.

M. Messadi, A. Bessaid And A. Taleb-Ahmed, "Extraction of specific parameters for skin tumour classification", *Journal of Medical Engineering & Technology*, Vol. 33, No. 4, May 2009, 288-295.

Riegel D S, "Epiluminescence microscopy in clinical diagnosis of pigmented skin lesions", *Lancet* 349:1566:1567, 1997.

Pietro Rubegni, et al., "Digital Dermoscopy Analysis and Artificial Neural Network for the Differentiation of Clinically Atypical Pigmented Skin Lesions: A Retrospective Study", *Journal Of Investigative Dermatology*, Vol. 119, No. 2, pp 471-474, August 2002.

Soyer H P, Smolle J, Kerl H, Steiner H, "Early diagnosis of malignant melanoma by surface microscopy", *Lancet* 2:803, 1987.

Tatiana Tommasi, Elisabetta La Torre, and Barbara Caputo, "Melanoma Recognition Using Representative and Discriminative Kernel Classifiers", in: *Lecture Notes in Computer Science*, vol. 4241. Springer, Berlin. pp. 1-12. 2006.

Ezzeddine Zagrouba and Walid Baroumi, A preliminary approach for the automated recognition of malignant melanoma. *Image Anal Stereal*, Vol. 23 121:135, 2004.

The invention claimed is:

1. A system for analyzing image data received from a remote user for evaluating a medical image for screening for a disease or condition, the system comprising:

a server in communication with a distributed network for receiving a digital image data sent from the remote user, the remote user also in communication with the distributed network;

a processor for executing a learning machine, wherein the learning machine is trained using image data sets having known outcomes for skin cancer, the processor further operable for:

receiving the digital image data set from the remote user;

pre-processing the digital image data set to extract features from the image;

inputting the extracted features into the trained learning machine to produce an output comprising a recognized pattern within the digital image data set;

post-processing the output to generate a score corresponding to the recognized pattern associated with the disease or condition; and transmitting the score to the server;

wherein the server is further operable for transmitting the score to the remote user across the distributed network.

2. The system of claim 1, wherein the server is further operable for transmitting information about the disease or condition to the remote user across the distributed network.

3. The system of claim 2, wherein the disease or condition is skin cancer.

4. The system of claim 1, wherein the digital image is generated by the remote user using a camera integrated into a smart phone and wherein the smart phone is in communication with the distributed network.

5. The system of claim 1, wherein the digital image is generated by the remote user using a digital camera and wherein the digital image is stored on a personal computer that is in communication with the distributed network.

6. The system of claim 1, wherein the server is further operable for generating a survey for completion by the remote user.

7. A system for analyzing image data received from a remote user for screening for skin cancer, the system comprising:

a server in communication with a distributed network for receiving a digital image data set from the remote user, the remote user also in communication with the distributed network;

a processor for executing a learning machine, wherein the learning machine is trained using image data sets having known outcomes for skin cancer, the processor further operable for:

receiving the digital image data set from the remote user;

pre-processing the digital image data set to extract features including contour, dimension and color features;

inputting the extracted features into the trained learning machine to produce an output comprising a recognized pattern within the digital image data set;

post-processing the output to generate a skin cancer risk score corresponding to the recognized pattern; and transmitting the skin cancer risk score to the server;

wherein the server is further operable for transmitting the alphanumerical skin cancer risk score to the remote user across the distributed network.

8. The system of claim 7, wherein the server is further operable for transmitting information about skin cancer to the remote user across the distributed network.

9. The system of claim 7, wherein the digital image is generated by the remote user using a camera integrated into a smart phone and wherein the smart phone is in communication with the distributed network.

10. The system of claim 7, wherein the digital image is generated by the remote user using a digital camera and wherein the digital image is stored on a personal computer that is in communication with the distributed network.

11. The system of claim 7, wherein the server is further operable for generating a survey for completion by the remote user.

12. The system of claim 7, further comprising a physician referral database, wherein the server is further operable for obtaining geographical location information from the remote user and matching physicians within the referral database with the remote user based upon the remote user's geographical location.

13. The system of claim 7, wherein preprocessing includes an algorithm for identification of garbage images that are unrelated to skin cancer.

* * * * *